(12) United States Patent
Khodadoust et al.

(10) Patent No.: US 6,558,936 B1
(45) Date of Patent: May 6, 2003

(54) HUMAN LIPASE PROTEINS, NUCLEIC ACIDS ENCODING THEM, AND USES OF BOTH OF THESE

(75) Inventors: Mehran Khodadoust, Chestnut Hill, MA (US); Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/411,132

(22) Filed: Oct. 1, 1999

(51) Int. Cl.[7] .................... C12N 9/20; C12N 15/00; C12N 5/00; C12Q 1/68; C07H 21/04
(52) U.S. Cl. ................ 435/198; 435/252.3; 435/325; 435/320.1; 435/6; 536/23.2
(58) Field of Search .............. 435/198, 252.3, 435/325, 6; 536/23.2

(56) References Cited

PUBLICATIONS

Giller et al. Database GenEmbl, Accession No. M93283, Jan. 1995, see the sequence alignment.*
Giller et al., 1992, J. Biol. Chem. 267:16509–16516.
Kerfelec et al., 1986, Pancreas 1:430–437.
Mickel et al., 1989, J. Biol. Chem. 264:12895–12901.
Wicker–Planquart et al., 1992, FEBS Lett. 296:61–66.
Remington et al., 1999, Invest. Ophthalmol. Vis. Sci. 40:1081.

* cited by examiner

Primary Examiner—M. Monshipouri
(74) Attorney, Agent, or Firm—Millennium Pharmaceuticals, Inc.

(57) ABSTRACT

The invention provides isolated nucleic acids encoding human lipase proteins and fragments, derivatives, and variants thereof. These nucleic acids and proteins are useful for diagnosis, prevention, and therapy of a number of human and other animal disorders associated, for example, with aberrant lipid metabolism or aberrant pancreatic activity. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides, and antibodies. Diagnostic, prognostic, screening, and therapeutic methods involving use of compositions of the invention are also provided. The nucleic acids and polypeptides of the present invention are useful as modulating agents in regulating a variety of cellular processes relating to mono-, di-, and triglyceride metabolism and pancreatic function.

23 Claims, 8 Drawing Sheets

```
        1                                                              60
MLip-1  MLGIWIVAFLFFGTSRGKEVCYERLGCFKDGLPWTRTFSTELVGLPWSPEKINTRFLLYT
hPL     MLIFWTITLFLLGAAKGKEVCYEDLGCFSDTEPWGGTAIRPLKILPWSPEKIGTRFLLYT
hPLRP1  MLPPWTLGLLLLATVRGKEVCYGQLGCFSDEKPWAGTLQRPVKLLPWSPEDIDTRFLLYT
hPLRP2  MLPLMTLSL-LLGAVAGKEVCYERLGCFSDDSPWSGITERPLHILPWSPKDVNTRFLLYT 61                                                             120
MLip-1  IHNPNAYQEISAVNSSTIQASYFGTDKITRINIAGW--KTDGKWQRDMCNVLLQLEDINC
hPL     NENPNNFQILLLSDPSTIEASNFQMDRKTRFIIHGFIDKGDESWVTDMCKKLFEVEEVNC
hPLRP1  NENPNNFQLITGTEPDTIEASNFQLDRKTRFIIHGFLDKAEDSWPSDMCKKMFEVEKVNC
hPLRP2  NENPNNFQEVA-ADSSSISGSNFKTNRKTRFIIHGFIDKGEENWLANVCKNLFKVESVNC 121                                                            180
MLip-1  INLDWINGSRE-YIHAVNNLRVVGAEVAYFIDVLMKKFEYSPSKVHLIGHSLGAHLAGEA
hPL     ICVDWKKGSQATYTQAANNVRVVGAQVAQMLDILLTEYSYPPSKVHLIGHSLGAHVAGEA
hPLRP1  ICVDWRHGSRAMYTQAVQNIRVVGAETAFLIQALSTQLGYSLEDVHVIGHSLGAHTAAEA
hPLRP2  ICVDWKGGSRTGYTQASQNIRIVGAEVAYFVEFLQSAFGYSPSNVHVIGHSLGAHAAGEA 181                                                            240
MLip-1  GSRIPG-LGRITGLDPAGPFFHNTPKEVRLDPSDANFVDVIHTNAARILFELGVGTIDAC
hPL     GSKTPG-LSRITGLDPVEASFESTPEEVRLDPSDADFVDVIHTDAAPLIPFLGFGTNQQM
hPLRP1  GRRLGGRVGRITGLDPAGPCFQDEPEEVRLDPSDAVFVDVIHTDSSPIVPSLGFGMSQKV
hPLRP2  GRRTNGTIGRITGLDPAEPCFQGTPELVRLDPSDAKFVDVIHTDGAPIVPNLGFGMSQVV
```

Fig. 1A

```
              241                                                        300
    MLip-1    GHLDFYPNGGKHMPGCEDLITPLLKFNFNAYKKEMASFFDCNHARSYQFYAESILNPDAF
    hPL       GHLDFFPNGGESMPGCKKNALSQIV-DLDGIWAGTRDFVACNHLRSYKYYLESILNPDGF
    hPLRP1    GHLDFFPNGGKEMPGCKKNVLSTIT-DIDGIWEGIGGFVSCNHLRSFEYYSSSVLNPDGF
    hPLRP2    GHLDFFPNGGVEMPGCKKNILSQIV-DIDGIWEGTRDFAACNHLRSYKYYTDSIVNPDGF 301                                                        360
    MLip-1    IAYPCRSYTSFKAGNCFFCSKEGCPTMGHFADRFHFKNMKTNGSHYFLNTGSLSPFARWR
    hPL       AAYPCTSYKSFESDKCFPCPDQGCPQMGHYADKFAGRT-SEEQQKFLNTGEASNFARWR
    hPLRP1    LGYPCASYDEFQESKCFPCPAEGCPKMGHYADQFKGKT-SAVEQTFFLNTGESGNFTSWR
    hPLRP2    AGFPCASYNVFTANKCFPCPSGGCPQMGHYADRYPGKT-NDVGQKFYLDTGDASNFARWR 361                                                        420
    MLip-1    HKLSVKLSGSEVTQGTVFLRVGGAIGKTGEFAIVSGKLEPGMTYTKLIDAEVNVGNITSV
    hPL       YGVSITLSGR-TATGQIKVALFGNKGNTHQYSIFRGILKPGSTHSYEFDAKLDVGTIEKV
    hPLRP1    YKVSVTLSGKEKVNGYIRIALYGSNENSKQYEIFKGSLKPDASHTCAIDVDFNVGKIQKV
    hPLRP2    YKVSVTLSGK-KVTGHILVSLFGNKGNSKQYEIFKGTLKPDSTHSNEFDSDVDVGDLQMV 421                                                        480
    MLip-1    QFIWKKHLFEDSQNKLGAEMVINTSGKYGYKSTFCSQDIMGPNILQNLKPC
    hPL       KFLWNNNVINPTLPKVGATKITVQKGEEKTVYNFCSEDTVR------EDTLLLTTPC
    hPLRP1    KFLMNKRGINLSEPKLGASQITVQSGEDGTEYNFCSSDTVEENVLQSLYPC
    hPLRP2    KFIWYNNVINPTLPRVGASKIIVETNVGKQ-FNFCSPETVREEVLLTLTPC
```

Fig. 1B

```
GGAATTCCCG GGTCGACCCA CGCGTCCGCA TTGTGAGGAA AACCACTTAG TATTTTATAG TGAGGTGACT
TTACAAGTAA AGATCTTCAA GAAGATTTTT ATGTGATTTA AAAAATCAGC TTAGATGCTT GGAATTTGGA
TTGTTGCATT CTTGTTCTTT GGCACATCAA GAGGAAAAGA AGTTTGCTAT GAAAGGTTAG GGTGTTTCAA
AGATGGTTTA CCATGGACCA GGACTTTCTC AACAGAGTTG GTAGGTTTAC CCTGGTCTCC AGAGAAGATA
AACACTCGTT TCCTGCTCTA CACTATACAC AATCCCAATG GTAGGTTTAC GATCAGTGCG GTTAATTCTT
CAACTATCCA AGCCTCATAT TTTGGAACAG ACAAGATCAC CCTATCAGGA ATAGCTGGAT GGAAAACAGA
TGGCAAATGG CAGAGAGACA TGTGCAATGT GTTGCTACAG CCGTATCAAC CTGGAAGATA TAAATTGCAT TAATTAGAT
TGGATCAACG GTTCACGGGA ATACATCCAT GCTGTAAACA CTGGAAGATA TGTTGGTGCT GAGGTGGCTT
ATTTTATTGA TGTTCTCATG AAAAATTTG AATATTCCCC TTCTAAAGTG CACTTGATTG GCCACAGCTT
GGGAGCACAC CTGGCTGGGG AAGCTGGGTC AAGGATACCA GCCCTTGGAA GAATAACTGG GTTGGACCCA
GCTGGGCCAT TTTTCCACAA CACTCCAAAG GAAGTCAGGC TAGACCCCTC GGATGCCAAC TTTGTTGACG
TTATTCATAC AAATGCAGCT CGCATCCTCT TTGAGCTTGG TGTTGGAACC ATTGATGCTT GTGGTCATCT
TGACTTTTAC CCAAATGGAG GGAAGCACAT GCCAGGATGT GAAGACTTAA TTACACCTTT ACTGAAATTT
AACTTCAATG CTTACAAAAA AGAAATGGCT TCCTTCTTTG ACTGTAACCA TGCCCGAAGT TATCAATTTT
ATGCTGAAAG CATTCTTAAT CCTGATGCAT TTATTGCTTA TCCTTGTAGA TCCTACACAT CTTTTAAAGC
AGGAAATTGC TTCTTTTGTT CCAAAGAAGG TTGCCCAACA ATGGGTCATT TTGCTGATAG ATTTCACTTC
AAAAATATGA AGACTAATAT ATCACATTAT TTTTAAAACA CAGGGTCCCT TTCCCCATTT GCCCGTTGGA
GGCACAAATT GTCTGTTAAA CTCAGTGGAA GCGAAGTCAC CAGGGAACT GTCTTTCTTC GTGTAGGCGG
GGCAATTGGG AAAACTGGGG AGTTTGCCAT TGTCAGTGGA AAACTTGAGC CAGGCATGAC TTACACAAAA
TTAATCGATG CAGAGGTTAA CGTTGGAAAC ATTACAAGTG TTCAGTTCAT CTGGAAAAAA CATTTGTTTG
AAGATTCTCA GAATAAGTTG GGAGCAGAAA TGGTGATAAA TACATCTGGG AAATATGGAT ATAAATCTAC
CTTCTGTAGC CAAGACATTA TGGGACCTAA TATTCTCCAG AACCTGAAAC CATGCTAATC TCAGATACAG
```

Fig. 2A

```
TCTTGATGGA  TTTCTTTAGT  AGGAGCAATG  AAGAAAAGTG  TCTCCTTCCA  CCTGGCATCC  AGACCAAATT
TGACCCTTGT  AAATGACTTA  GTCATTTACA  AGGGTCTTAC  TCAGAGTCAA  GTACGGGTTT  GCTTTTTTTC
TGTGTAGAAT  GTTCATCTAA  CTGCACCTTA  AAAACACACT  GAACCCTGGG  ACAAAAGATA  ATTACTATGA
TCTGTAGGAA  TCTGGATATC  ATTGACAAAA  TAGAGCTGTT  TTGGAATTTT  CCTGAATAAG  AGGAGGTGAT
GCAAATGTAT  GTTGAGTGTA  TAAACTCACT  GGACAAAAGT  AAGCCTCTGG  CTTGCTGAGT  TTTTGAAGTA
TATTTCAGG   TATAATAAAT  ATTGTTCTAA  AATTATATAA  AACTATTTGT  TATGTTGTTA  AATCTTGCTG
AGACAAATTA  TGACTATAGT  GCATGATATA  TAGTAGATTA  TAACCTTGTG  GGTTGATGTG  TCTATCTAGT
AATATAAAA   ACTAATGAGA  TGGCACTAGT  ATTTCCAAGG  TGTTCCTTGG  TGTTCAGGGT  GTGCCCAAGA
GAGATTTGG   AGCTTATCTG  TTATGTGTTC  ATCAGTTAGC  AATGGGACCT  GAAGTTCANC  AACCCAGGGT
ATAGCCCCCT  TCCTCCAAAG  TCCCTGCCAC  AGGAGAATTA  CTCCTCTCTC  TGGGTCTTGA  ATGCTCTATG
GTGAATTTGT  ATTAGCCCTC  AAGGCAGCAT  TTCATTTGTA  AGCACTTGG   GTAACCCTTT  GTTCTTNCAA
TANCAATATT  ATAATATTTA  AATATGAAAA  AAAAAAAAAAA  AA
```

Fig. 2B

```
MLGIWIVAFL  FFGTSRGKEV  CYERLGCFKD  GLPWTRTFST  ELVGLPWSPE  KINTRFLLYT  IHNPNAYQEI
SAVNSSTIQA  SYFGTDKITR  INIAGWKTDG  KWQRDMCNVL  LQLEDINCIN  LDWINGSREY  IHAVNNLRVV
GAEVAYFIDV  LMKKFEYSPS  KVHLIGHSLG  AHLAGEAGSR  IPGLGRITGL  DPAGPFFHNT  PKEVRLDPSD
ANFVDVIHTN  AARILFELGV  GTIDACGHLD  FYPNGGKHMP  GCEDLITPLL  KFNFNAYKKE  MASFFDCNHA
RSYQFYAESI  LNPDAFIAYP  CRSYTSFKAG  NCFFCSKEGC  PTMGHFADRF  HFKNMKTNGS  HYFLNTGSLS
PFARWRHKLS  VKLSGSEVTQ  GTVFLRVGGA  IGKTGEFAIV  SGKLEPGMTY  TKLIDAEVNV  GNITSVQFIW
KKHLFEDSQN  KLGAEMVINT  SGKYGYKSTF  CSQDIMGPNI  LQNLKPC
```

Fig. 2C

```
          1
MLip-1    MLGIWIVAFLFFGTSRGKEVCYERLGCFKDGLPWTRTFSTELVGLPWSPEKINTRFLLYT
MPLRP1    MLILWTIPLFLLGAAQGKEVCYDNLGCFSDAEPWAGTAIRPLKLLPWSPEKINTRFLLYT
RPLRP1p   MLTLWTVSLFLLGAAQGKEVCYDNLGCFSDAEPWAGTAIRPLKLLPWSPEKINTRFLLYT
CPTLP     MVSIWTIALFLLGAAKAKEVCYEQIGCFSDAEPWAGTAIRPLKVLPWSPERIGTRFLLYT
CPLRP1p   MVSIWTIALFLLGAAKAKEVCYEQIGCFSDAEPWAGTAIRPLKVLPWSPERIGTRFLLYT 61                                                          120
MLip-1    IHNPNAYQEISAVNSSTIQASYFGTDKITRINIAGW--KTDGKWQRDMCNVLLQLEDINC
MPLRP1    NENPTAFQTLQLSDPSTIEASNFQVARKTRFIIHGFIDKGEENWVVDMCKNMFQVEEVNC
RPLRP1p   NENPTAFQTLQLSDPLTIGASNFQVARKTRFIIHGFIDKGEENWVVDMCKNMFQVEEVNC
CPTLP     NKNPNNFQTLLPSDPSTIEASNFQTDKKTRFTIHGFINKGEENWLLDMCKNMFKVEEVNC
CPLRP1p   NKNPNNFQTLLPSDPSTIEASNFQTDKKTRFIIHGFIDKGEENWLLDMCKNMFKVEEVNC 121                                                         180
MLip-1    INLDWINGSRE-YIHAVNNLRVVGAEVAYFIDVLMKKFEYSPSKVHLIGHSLGAHLAGEA
MPLRP1    ICVDWKRGSQTTYTQAANNVRVVGAQVAQMIDILVRNFNYSASKVHLIGHSLGAHVAGEA
RPLRP1p   ICVDWKKGSQTTYTQAANNVRVVGAQVAQMIDILVKNYSYSPSKVHLIGHSLGAHVAGEA
CPTLP     ICVDWKKGSQTSYTQAANNVRVVGAQVAQMLSMLSANYSYSPSQVLIGHSLGAHVAGEA
CPLRP1p   ICVDWKKGSQTSYTQAANNVRVVGAQVAQMLSMLSANYSYSPSQVLIGHSLGAHVAGEA
```

Fig. 3A

```
        181                                                            240
MLip-1  GSRIPGLGRITGLDPAGPFFHNTPKEVRLDPSDANFVDVIHTNAARILFELGVGTIDACG
MPLRP1  GSRTPGLGRITGLDPVEANFEGTPEEVRLDPSDADFVDVIHTDAAPLIPFLGFGTNQMVG
RPLRP1p GSRTPGLGRITGLDPVEANFEGTPEEVRLDPSDADFVDVIHTDAAPLIPFLGFGTNQMSG
CPTLP   GSRTPGLGRITGLDPVEASFQGTPEEVRLDPTDADFVDVIHTDAAPLIPFLGFGTSQQMG
CPLRP1p GSRTPGLGRITGLDPVEASFQGTPEEVRLDPTDADFVDVIHTDAAPLIPFLGFGTSQQMG 241                                                            300
MLip-1  HLDFYPNGGKHMPGCEDLITPLLKFNFNAYKKEMASFFDCNHARSYQFYAESILNPDAFI
MPLRP1  HFDFFPNGGQYMPGCKKNALSQI-VDIDGIWSGTRDFVACNHLRSYKYLESILNPDGFA
RPLRP1p HLDFFPNGGQSMPGCKKNALSQI-VDIDGIWSGTRDFVACNHLRSYKYYLESILNPDGFA
CPTLP   HLDFFPNGGEEMPGCKKNALSQI-VNLDGIWEGTRDFVACNHLRSYKYKYSESILNPDGFA
CPLRP1p HLDFFPNGGEEMPGCKKNALSQI-VDLDGIWEGTRDFVACNHLRSYKYYSESILNPDGFA 301                                                            360
MLip-1  AYPCRSYTSFKAGNCFFCSKEGCPTMGHFADRFHFKNMKTNGSHYFLNTGSLSPFARWRH
MPLRP1  AYPCASYRDFESNKCFPCPDQGCPQMGHYADKFANNT-SVEPQKFFLNTGEAKNFARWRY
RPLRP1p AYPCASYKDFESNKCFPCPDQGCPQMGHYADKFAGKS-GDEPQKFFLNTGEAKNFARWRY
CPTLP   SYPCASYRAFESNKCFPCPDQGCPQMGHYADKFAVKT-SDETQKYFLNTGDSSNFARWRY
CPLRP1p SYPCASYRAFESNKCFPCPDQGCPQMGHYADKFAVKT-SDETQKYFLNTGDSSNFARWRY
```

Fig. 3B

```
       361                                                              420
MLip-1 KLSVKLSGSEVTQGTVFLRVGGAIGKTGEFAIVSGKLEPGMTYTKLIDAEVNVGNITSVQ
MPLRP1 RVSLTFSGRTVT-GQVKVSLFGSNGNTRQCDIFRGIIKPGATHSNEFDAKLDVGTIEKVK
RPLRP1p RVSLILSGRMVT-GQVKVALFGSKGNTRQYDIFRGIIKPGATHSSEFDAKLDVGTIEKVK
CPTLP  GVSITLSGKRAT-GQAKVALFGSKGNTHQFNIFKGILKPGSTHSNEFDAKLDVGTIEKVK
CPLRP1p GVSITLSGKRAT-GQAKVALFGSKGNTHQFNIFKGILKPGSTHSNEFDAKLDVGTIEKVK 421                                                       476
MLip-1 FIWKKHLFEDSQNKLGAEMVINTSGKYGYKSTFCSQDIMGPNILQNLKPC
MPLRP1 FLWNNHVVNPSFPKVGAAKITVQKGEERTEHNFCSEETVREDILLTLLPCKTSDTM
RPLRP1p FLWNNQVINPSFPKVGAAKITVQKGEERTEYNFCSEETVREDTLLTLLPCETSDTV
CPTLP  FLWNNNVVNPTFPKVGAAKITVQKGEEKTVHSFCSESTVREDVLLTLTPC
CPLRP1p FLWNNNVVNPTFPKVGAAKITVQKGEEKTVHSFCSESTVREDVLLTLTPC
```

Fig. 3C

SEQUENCE LISTING

```
<160> NUMBER OF SEQ ID NOS:  10

<210> SEQ ID NO 1
<211> LENGTH: 2352
<212> TYPE: DNA
<213> ORGANISM: Homo sapiens
<220> FEATURE:
<221> NAME/KEY: unsure
<222> LOCATION: (2159)
<221> NAME/KEY: unsure
<222> LOCATION: (2307)
<221> NAME/KEY: unsure
<222> LOCATION: (2313)

<400> SEQUENCE: 1
ggaattcccg ggtcgaccca cgcgtccgca ttgtgaggaa aaccacttag tattttatag      60
tgaggtgact ttacaagtaa agatcttcaa gaagattttt atgtgattta aaaaatcagc     120
ttagatgctt ggaatttgga ttgttgcatt cttgttcttt ggcacatcaa gaggaaaaga     180
agtttgctat gaaaggttag ggtgtttcaa agatggttta ccatggacca ggactttctc     240
aacagagttg gtaggtttac cctggtctcc agagaagata aacactcgtt tcctgctcta     300
cactatacac aatcccaatg cctatcagga gatcagtgcg gttaattctt caactatcca     360
agcctcatat tttggaacag acaagatcac ccgtatcaac atagctggat ggaaaacaga     420
tggcaaatgg cagagagaca tgtgcaatgt gttgctacag ctggaagata taaattgcat     480
taatttagat tggatcaacg gttcacggga atacatccat gctgtaaaca atctccgtgt     540
tgttggtgct gaggtggctt attttattga tgttctcatg aaaaaatttg aatattcccc     600
```

-continued

```
ttctaaagtg cacttgattg gccacagctt gggagcacac ctggctgggg aagctgggtc      660
aaggatacca ggccttggaa gaataactgg gttggaccca gctgggccat ttttccacaa      720
cactccaaag gaagtcaggc tagacccctc ggatgccaac tttgttgacg ttattcatac      780
aaatgcagct cgcatcctct tgagcttgg  tgttggaacc attgatgctt gtggtcatct      840 tgactttttac ccaaatggag ggaagcacat gccaggatgt gaagacttaa ttacaccttt     900
actgaaattt aacttcaatg cttacaaaaa agaaatggct ccttctttg actgtaacca       960 tgcccgaagt tatcaatttt atgctgaaag cattcttaat cctgatgcat ttattgctta    1020
tccttgtaga tcctacacat cttttaaagc aggaaattgc ttcttttgtt ccaaagaagg    1080
ttgcccaaca atgggtcatt tgctgatag  atttcacttc aaaatatga agactaatgg     1140 atcacattat ttttttaaaca cagggtccct ttccccattt gcccgttgga ggcacaaatt   1200
gtctgttaaa ctcagtggaa gcgaagtcac tcaaggaact gtctttcttc gtgtaggcgg    1260
ggcaattggg aaaactgggg agtttgccat tgtcagtgga aaacttgagc caggcatgac    1320
ttacacaaaa ttaatcgatg cagaggttaa cgttggaaac attacaagtg ttcagttcat    1380
ctggaaaaaa catttgtttg aagattctca gaataagttg ggagcagaaa tggtgataaa    1440
tacatctggg aaatatggat ataaatctac cttctgtagc aagacatta  tgggacctaa    1500 tattctccag aacctgaaac catgctaatc tcagatacag tcttgatgga tttctttagt    1560
aggagcaatg aagaaaagtg tctccttcca cctggcatcc agaccaaatt tgacccttgt   1620
aaatgactta gtcatttaca agggtcttac tcagagtcaa gtacgggttt gcttttttc    1680 tgtgtagaat gttcatctaa ctgcacctta aaaacacact gaaccctggg acaaaagata    1740
attactatga tctgtaggaa tctggatatc attgacaaaa tagagctgtt ttggaatttt    1800
cctgaataag aggaggtgat gcaaatgtat gttgagtgta taaactcact ggacaaaagt    1860
aagcctctgg cttgctgagt ttttgaagta tattttcagg tataataatc attgttctaa    1920
aattatataa aactatttgt tatgttgtta aatcttgctg agacaaatta tgactatagt    1980
gcatgatata tagtagatta taaccttgtg ggttgatgtg tctatctagt aataataaaa    2040
actaatgaga tggcactagt atttccaagg tgttccttgg tgttcagggt gtgcccaaga    2100
gagattttgg agcttatctg ttatgtgttc atcagttagc aatgggacct gaagttcanc    2160
aacccagggt atagcccct  tcctccaaag tccctgccac aggagaatta ctcctctctc    2220
tgggtcttga atgctctatg gtgaatttgt atttagcctc aaggcagcat ttcatttgta    2280
aagcacttgg gtaacccttt gttcttncaa tancaatatt ataatattta aatatgaaaa    2340
aaaaaaaaaa aa                                                         2352
```

```
<210> SEQ ID NO 2
<211> LENGTH: 1401
<212> TYPE: DNA
<213> ORGANISM: Homo sapiens

<400> SEQUENCE: 2
atgcttggaa tttggattgt tgcattcttg ttctttggca catcaagagg aaaagaagtt       60
tgctatgaaa ggttagggtg tttcaaagat ggtttaccat ggaccaggac tttctcaaca      120
gagttggtag gtttaccctg gtctccagag aagataaaca ctcgtttcct gctctacact      180
atacacaatc ccaatgccta tcaggagatc agtgcggtta attcttcaac tatccaagcc      240
tcatattttg gaacagacaa gatcacccgt atcaacatag ctggatggaa aacagatggc      300
```

-continued

```
aaatggcaga gagacatgtg caatgtgttg ctacagctgg aagatataaa ttgcattaat    360
ttagattgga tcaacggttc acgggaatac atccatgctg taaacaatct ccgtgttgtt    420
ggtgctgagg tggcttattt tattgatgtt ctcatgaaaa aatttgaata ttcccttct     480
aaagtgcact tgattggcca cagcttggga gcacacctgg ctggggaagc tgggtcaagg    540
ataccaggcc ttggaagaat aactgggttg gacccagctg gccatttttt ccacaacact    600
ccaaaggaag tcaggctaga cccctcggat gccaactttg ttgacgttat tcatacaaat    660
gcagctcgca tcctctttga gcttggtgtt ggaaccattg atgcttgtgg tcatcttgac    720
tttacccaa atggagggaa gcacatgcca ggatgtgaag acttaattac acctttactg     780
aaatttaact tcaatgctta caaaaaagaa atggcttcct tctttgactg taaccatgcc    840
cgaagttatc aattttatgc tgaaagcatt cttaatcctg atgcatttat tgcttatcct    900
tgtagatcct acacatcttt taaagcagga aattgcttct tttgttccaa agaaggttgc    960
ccaacaatgg gtcattttgc tgatagattt cacttcaaaa atatgaagac taatggatca   1020
cattattttt taaacacagg gtccctttcc ccatttgccc gttggaggca caaattgtct   1080
gttaaactca gtggaagcga agtcactcaa ggaactgtct tcttcgtgt aggcggggca    1140
attgggaaaa ctggggagtt tgccattgtc agtggaaaac ttgagccagg catgacttac   1200
acaaaattaa tcgatgcaga ggttaacgtt ggaaacatta caagtgttca gttcatctgg   1260
aaaaaacatt tgtttgaaga ttctcagaat aagttgggag cagaaatggt gataaataca   1320
tctgggaaat atggatataa atctaccttc tgtagccaag acattatggg acctaatatt   1380
ctccagaacc tgaaaccatg c                                             1401
```

<210> SEQ ID NO 3
<211> LENGTH: 467
<212> TYPE: PRT
<213> ORGANISM: Homo sapiens

<400> SEQUENCE: 3

```
Met Leu Gly Ile Trp Ile Val Ala Phe Leu Phe Phe Gly Thr Ser Arg
  1               5                  10                  15

Gly Lys Glu Val Cys Tyr Glu Arg Leu Gly Cys Phe Lys Asp Gly Leu
             20                  25                  30

Pro Trp Thr Arg Thr Phe Ser Thr Glu Leu Val Gly Leu Pro Trp Ser
         35                  40                  45

Pro Glu Lys Ile Asn Thr Arg Phe Leu Leu Tyr Thr Ile His Asn Pro
     50                  55                  60

Asn Ala Tyr Gln Glu Ile Ser Ala Val Asn Ser Ser Thr Ile Gln Ala
 65                  70                  75                  80

Ser Tyr Phe Gly Thr Asp Lys Ile Thr Arg Ile Asn Ile Ala Gly Trp
                 85                  90                  95

Lys Thr Asp Gly Lys Trp Gln Arg Asp Met Cys Asn Val Leu Leu Gln
            100                 105                 110

Leu Glu Asp Ile Asn Cys Ile Asn Leu Asp Trp Ile Asn Gly Ser Arg
        115                 120                 125

Glu Tyr Ile His Ala Val Asn Asn Leu Arg Val Val Gly Ala Glu Val
    130                 135                 140

Ala Tyr Phe Ile Asp Val Leu Met Lys Lys Phe Glu Tyr Ser Pro Ser
145                 150                 155                 160

Lys Val His Leu Ile Gly His Ser Leu Gly Ala His Leu Ala Gly Glu
                165                 170                 175
```

-continued

Ala Gly Ser Arg Ile Pro Gly Leu Gly Arg Ile Thr Gly Leu Asp Pro
            180                 185                 190

Ala Gly Pro Phe Phe His Asn Thr Pro Lys Glu Val Arg Leu Asp Pro
            195                 200                 205

Ser Asp Ala Asn Phe Val Asp Val Ile His Thr Asn Ala Ala Arg Ile
            210                 215                 220

Leu Phe Glu Leu Gly Val Gly Thr Ile Asp Ala Cys Gly His Leu Asp
225                 230                 235                 240

Phe Tyr Pro Asn Gly Gly Lys His Met Pro Gly Cys Glu Asp Leu Ile
            245                 250                 255

Thr Pro Leu Leu Lys Phe Asn Phe Asn Ala Tyr Lys Lys Glu Met Ala
            260                 265                 270

Ser Phe Phe Asp Cys Asn His Ala Arg Ser Tyr Gln Phe Tyr Ala Glu
            275                 280                 285

Ser Ile Leu Asn Pro Asp Ala Phe Ile Ala Tyr Pro Cys Arg Ser Tyr
            290                 295                 300

Thr Ser Phe Lys Ala Gly Asn Cys Phe Phe Cys Ser Lys Glu Gly Cys
305                 310                 315                 320

Pro Thr Met Gly His Phe Ala Asp Arg Phe His Phe Lys Asn Met Lys
            325                 330                 335

Thr Asn Gly Ser His Tyr Phe Leu Asn Thr Gly Ser Leu Ser Pro Phe
            340                 345                 350

Ala Arg Trp Arg His Lys Leu Ser Val Lys Leu Ser Gly Ser Glu Val
            355                 360                 365

Thr Gln Gly Thr Val Phe Leu Arg Val Gly Ala Ile Gly Lys Thr
            370                 375                 380

Gly Glu Phe Ala Ile Val Ser Gly Lys Leu Glu Pro Gly Met Thr Tyr
385                 390                 395                 400

Thr Lys Leu Ile Asp Ala Glu Val Asn Val Gly Asn Ile Thr Ser Val
            405                 410                 415

Gln Phe Ile Trp Lys Lys His Leu Phe Glu Asp Ser Gln Asn Lys Leu
            420                 425                 430

Gly Ala Glu Met Val Ile Asn Thr Ser Gly Lys Tyr Gly Tyr Lys Ser
            435                 440                 445

Thr Phe Cys Ser Gln Asp Ile Met Gly Pro Asn Ile Leu Gln Asn Leu
            450                 455                 460

Lys Pro Cys
465

<210> SEQ ID NO 4
<211> LENGTH: 467
<212> TYPE: PRT
<213> ORGANISM: Homo sapiens

<400> SEQUENCE: 4

Met Leu Ile Phe Trp Thr Ile Thr Leu Phe Leu Leu Gly Ala Ala Lys
1               5                   10                  15

Gly Lys Glu Val Cys Tyr Glu Asp Leu Gly Cys Phe Ser Asp Thr Glu
            20                  25                  30

Pro Trp Gly Gly Thr Ala Ile Arg Pro Leu Lys Ile Leu Pro Trp Ser
            35                  40                  45

Pro Glu Lys Ile Gly Thr Arg Phe Leu Leu Tyr Thr Asn Glu Asn Pro
        50                  55                  60

Asn Asn Phe Gln Ile Leu Leu Leu Ser Asp Pro Ser Thr Ile Glu Ala
65                  70                  75                  80

```
Ser Asn Phe Gln Met Asp Arg Lys Thr Arg Phe Ile Ile His Gly Phe
                 85                  90                  95
Ile Asp Lys Gly Asp Glu Ser Trp Val Thr Asp Met Cys Lys Lys Leu
            100                 105                 110
Phe Glu Val Glu Val Asn Cys Ile Cys Val Asp Trp Lys Lys Gly
            115                 120                 125
Ser Gln Ala Thr Tyr Thr Gln Ala Ala Asn Val Arg Val Val Gly
        130                 135                 140
Ala Gln Val Ala Gln Met Leu Asp Ile Leu Leu Thr Glu Tyr Ser Tyr
145                 150                 155                 160
Pro Pro Ser Lys Val His Leu Ile Gly His Ser Leu Gly Ala His Val
                165                 170                 175
Ala Gly Glu Ala Gly Ser Lys Thr Pro Gly Leu Ser Arg Ile Thr Gly
            180                 185                 190
Leu Asp Pro Val Glu Ala Ser Phe Glu Ser Thr Pro Glu Glu Val Arg
        195                 200                 205
Leu Asp Pro Ser Asp Ala Asp Phe Val Asp Val Ile His Thr Asp Ala
        210                 215                 220
Ala Pro Leu Ile Pro Phe Leu Gly Phe Gly Thr Asn Gln Gln Met Gly
225                 230                 235                 240
His Leu Asp Phe Phe Pro Asn Gly Gly Glu Ser Met Pro Gly Cys Lys
                245                 250                 255
Lys Asn Ala Leu Ser Gln Ile Val Asp Leu Asp Gly Ile Trp Ala Gly
            260                 265                 270
Thr Arg Asp Phe Val Ala Cys Asn His Leu Arg Ser Tyr Lys Tyr Tyr
        275                 280                 285
Leu Glu Ser Ile Leu Asn Pro Asp Gly Phe Ala Ala Tyr Pro Cys Thr
        290                 295                 300
Ser Tyr Lys Ser Phe Glu Ser Asp Lys Cys Phe Pro Cys Pro Asp Gln
305                 310                 315                 320
Gly Cys Pro Gln Met Gly His Tyr Ala Asp Lys Phe Ala Gly Arg Thr
                325                 330                 335
Ser Glu Glu Gln Gln Lys Phe Phe Leu Asn Thr Gly Glu Ala Ser Asn
            340                 345                 350
Phe Ala Arg Trp Arg Tyr Gly Val Ser Ile Thr Leu Ser Gly Arg Thr
        355                 360                 365
Ala Thr Gly Gln Ile Lys Val Ala Leu Phe Gly Asn Lys Gly Asn Thr
        370                 375                 380
His Gln Tyr Ser Ile Phe Arg Gly Ile Leu Lys Pro Gly Ser Thr His
385                 390                 395                 400
Ser Tyr Glu Phe Asp Ala Lys Leu Asp Val Gly Thr Ile Glu Lys Val
                405                 410                 415
Lys Phe Leu Trp Asn Asn Asn Val Ile Asn Pro Thr Leu Pro Lys Val
            420                 425                 430
Gly Ala Thr Lys Ile Thr Val Gln Lys Gly Glu Glu Lys Thr Val Tyr
        435                 440                 445
Asn Phe Cys Ser Glu Asp Thr Val Arg Glu Asp Thr Leu Leu Thr Leu
        450                 455                 460
Thr Pro Cys
465

<210> SEQ ID NO 5
<211> LENGTH: 469
```

-continued

```
<212> TYPE: PRT
<213> ORGANISM: Homo sapiens

<400> SEQUENCE: 5

Met Leu Pro Pro Trp Thr Leu Gly Leu Leu Leu Ala Thr Val Arg
 1               5                  10                  15

Gly Lys Glu Val Cys Tyr Gly Gln Leu Gly Cys Phe Ser Asp Glu Lys
                20                  25                  30

Pro Trp Ala Gly Thr Leu Gln Arg Pro Val Lys Leu Leu Pro Trp Ser
         35                  40                  45

Pro Glu Asp Ile Asp Thr Arg Phe Leu Tyr Thr Asn Glu Asn Pro
     50                  55                  60

Asn Asn Phe Gln Leu Ile Thr Gly Thr Glu Pro Asp Thr Ile Glu Ala
 65                  70                  75                  80

Ser Asn Phe Gln Leu Asp Arg Lys Thr Arg Phe Ile Ile His Gly Phe
                 85                  90                  95

Leu Asp Lys Ala Glu Asp Ser Trp Pro Ser Asp Met Cys Lys Lys Met
            100                 105                 110

Phe Glu Val Glu Lys Val Asn Cys Ile Cys Val Asp Trp Arg His Gly
        115                 120                 125

Ser Arg Ala Met Tyr Thr Gln Ala Val Gln Asn Ile Arg Val Val Gly
    130                 135                 140

Ala Glu Thr Ala Phe Leu Ile Gln Ala Leu Ser Thr Gln Leu Gly Tyr
145                 150                 155                 160

Ser Leu Glu Asp Val His Val Ile Gly His Ser Leu Gly Ala His Thr
                165                 170                 175

Ala Ala Glu Ala Gly Arg Arg Leu Gly Gly Arg Val Gly Arg Ile Thr
            180                 185                 190

Gly Leu Asp Pro Ala Gly Pro Cys Phe Gln Asp Glu Pro Glu Glu Val
        195                 200                 205

Arg Leu Asp Pro Ser Asp Ala Val Phe Val Asp Val Ile His Thr Asp
    210                 215                 220

Ser Ser Pro Ile Val Pro Ser Leu Gly Phe Gly Met Ser Gln Lys Val
225                 230                 235                 240

Gly His Leu Asp Phe Phe Pro Asn Gly Gly Lys Glu Met Pro Gly Cys
                245                 250                 255

Lys Lys Asn Val Leu Ser Thr Ile Thr Asp Ile Asp Gly Ile Trp Glu
            260                 265                 270

Gly Ile Gly Gly Phe Val Ser Cys Asn His Leu Arg Ser Phe Glu Tyr
        275                 280                 285

Tyr Ser Ser Val Leu Asn Pro Asp Gly Phe Leu Gly Tyr Pro Cys
    290                 295                 300

Ala Ser Tyr Asp Glu Phe Gln Glu Ser Lys Cys Phe Pro Cys Pro Ala
305                 310                 315                 320

Glu Gly Cys Pro Lys Met Gly His Tyr Ala Asp Gln Phe Lys Gly Lys
                325                 330                 335

Thr Ser Ala Val Glu Gln Thr Phe Phe Leu Asn Thr Gly Glu Ser Gly
            340                 345                 350

Asn Phe Thr Ser Trp Arg Tyr Lys Val Ser Val Thr Leu Ser Gly Lys
        355                 360                 365

Glu Lys Val Asn Gly Tyr Ile Arg Ile Ala Leu Tyr Gly Ser Asn Glu
    370                 375                 380

Asn Ser Lys Gln Tyr Glu Ile Phe Lys Gly Ser Leu Lys Pro Asp Ala
385                 390                 395                 400
```

```
Ser His Thr Cys Ala Ile Asp Val Asp Phe Asn Val Gly Lys Ile Gln
                405                 410                 415
Lys Val Lys Phe Leu Trp Asn Lys Arg Gly Ile Asn Leu Ser Glu Pro
            420                 425                 430
Lys Leu Gly Ala Ser Gln Ile Thr Val Gln Ser Gly Glu Asp Gly Thr
        435                 440                 445
Glu Tyr Asn Phe Cys Ser Ser Asp Thr Val Glu Glu Asn Val Leu Gln
    450                 455                 460
Ser Leu Tyr Pro Cys
465

<210> SEQ ID NO 6
<211> LENGTH: 465
<212> TYPE: PRT
<213> ORGANISM: Homo sapiens

<400> SEQUENCE: 6

Met Leu Pro Leu Trp Thr Leu Ser Leu Leu Gly Ala Val Ala Gly
  1               5                  10                  15
Lys Glu Val Cys Tyr Glu Arg Leu Gly Cys Phe Ser Asp Asp Ser Pro
             20                  25                  30
Trp Ser Gly Ile Thr Glu Arg Pro Leu His Ile Leu Pro Trp Ser Pro
         35                  40                  45
Lys Asp Val Asn Thr Arg Phe Leu Leu Tyr Thr Asn Glu Asn Pro Asn
     50                  55                  60
Asn Phe Gln Glu Val Ala Ala Asp Ser Ser Ile Ser Gly Ser Asn
 65                  70                  75                  80
Phe Lys Thr Asn Arg Lys Thr Arg Phe Ile Ile His Gly Phe Ile Asp
                 85                  90                  95
Lys Gly Glu Glu Asn Trp Leu Ala Asn Val Cys Lys Asn Leu Phe Lys
            100                 105                 110
Val Glu Ser Val Asn Cys Ile Cys Val Asp Trp Lys Gly Gly Ser Arg
        115                 120                 125
Thr Gly Tyr Thr Gln Ala Ser Gln Asn Ile Arg Ile Val Gly Ala Glu
    130                 135                 140
Val Ala Tyr Phe Val Glu Phe Leu Gln Ser Ala Phe Gly Tyr Ser Pro
145                 150                 155                 160
Ser Asn Val His Val Ile Gly His Ser Leu Gly Ala His Ala Ala Gly
                165                 170                 175
Glu Ala Gly Arg Arg Thr Asn Gly Thr Ile Gly Arg Ile Thr Gly Leu
            180                 185                 190
Asp Pro Ala Glu Pro Cys Phe Gln Gly Thr Pro Glu Leu Val Arg Leu
        195                 200                 205
Asp Pro Ser Asp Ala Lys Phe Val Asp Val Ile His Thr Asp Gly Ala
    210                 215                 220
Pro Ile Val Pro Asn Leu Gly Phe Gly Met Ser Gln Val Val Gly His
225                 230                 235                 240
Leu Asp Phe Phe Pro Asn Gly Gly Val Glu Met Pro Gly Cys Lys Lys
                245                 250                 255
Asn Ile Leu Ser Gln Ile Val Asp Ile Asp Gly Ile Trp Glu Gly Thr
            260                 265                 270
Arg Asp Phe Ala Ala Cys Asn His Leu Arg Ser Tyr Lys Tyr Tyr Thr
        275                 280                 285
Asp Ser Ile Val Asn Pro Asp Gly Phe Ala Gly Phe Pro Cys Ala Ser
```

```
                290                 295                 300
Tyr Asn Val Phe Thr Ala Asn Lys Cys Phe Pro Cys Pro Ser Gly Gly
305                 310                 315                 320

Cys Pro Gln Met Gly His Tyr Ala Asp Arg Tyr Pro Gly Lys Thr Asn
                325                 330                 335

Asp Val Gly Gln Lys Phe Tyr Leu Asp Thr Gly Asp Ala Ser Asn Phe
                340                 345                 350

Ala Arg Trp Arg Tyr Lys Val Ser Val Thr Leu Ser Gly Lys Lys Val
                355                 360                 365

Thr Gly His Ile Leu Val Ser Leu Phe Gly Asn Lys Gly Asn Ser Lys
                370                 375                 380

Gln Tyr Glu Ile Phe Lys Gly Thr Leu Lys Pro Asp Ser Thr His Ser
385                 390                 395                 400

Asn Glu Phe Asp Ser Asp Val Asp Val Gly Asp Leu Gln Met Val Lys
                405                 410                 415

Phe Ile Trp Tyr Asn Asn Val Ile Asn Pro Thr Leu Pro Arg Val Gly
                420                 425                 430

Ala Ser Lys Ile Ile Val Glu Thr Asn Val Gly Lys Gln Phe Asn Phe
                435                 440                 445

Cys Ser Pro Glu Thr Val Arg Glu Glu Val Leu Leu Thr Leu Thr Pro
                450                 455                 460

Cys
465

<210> SEQ ID NO 7
<211> LENGTH: 473
<212> TYPE: PRT
<213> ORGANISM: Mus musculus

<400> SEQUENCE: 7

Met Leu Ile Leu Trp Thr Ile Pro Leu Phe Leu Leu Gly Ala Ala Gln
  1               5                  10                  15

Gly Lys Glu Val Cys Tyr Asp Asn Leu Gly Cys Phe Ser Asp Ala Glu
                 20                  25                  30

Pro Trp Ala Gly Thr Ala Ile Arg Pro Leu Lys Leu Leu Pro Trp Ser
                 35                  40                  45

Pro Glu Lys Ile Asn Thr Arg Phe Leu Leu Tyr Thr Asn Glu Asn Pro
             50                  55                  60

Thr Ala Phe Gln Thr Leu Gln Leu Ser Asp Pro Ser Thr Ile Glu Ala
 65                  70                  75                  80

Ser Asn Phe Gln Val Ala Arg Lys Thr Arg Phe Ile Ile His Gly Phe
                 85                  90                  95

Ile Asp Lys Gly Glu Glu Asn Trp Val Val Asp Met Cys Lys Asn Met
                100                 105                 110

Phe Gln Val Glu Glu Val Asn Cys Ile Cys Val Asp Trp Lys Arg Gly
                115                 120                 125

Ser Gln Thr Thr Tyr Thr Gln Ala Ala Asn Asn Val Arg Val Val Gly
                130                 135                 140

Ala Gln Val Ala Gln Met Ile Asp Ile Leu Val Arg Asn Phe Asn Tyr
145                 150                 155                 160

Ser Ala Ser Lys Val His Leu Ile Gly His Ser Leu Gly Ala His Val
                165                 170                 175

Ala Gly Glu Ala Gly Ser Arg Thr Pro Gly Leu Gly Arg Ile Thr Gly
                180                 185                 190
```

-continued

```
Leu Asp Pro Val Glu Ala Asn Phe Glu Gly Thr Pro Glu Val Arg
    195                 200                 205
Leu Asp Pro Ser Asp Ala Asp Phe Val Asp Val Ile His Thr Asp Ala
    210                 215                 220
Ala Pro Leu Ile Pro Phe Leu Gly Phe Gly Thr Asn Gln Met Val Gly
225                 230                 235                 240
His Phe Asp Phe Pro Asn Gly Gly Gln Tyr Met Pro Gly Cys Lys
                245                 250                 255
Lys Asn Ala Leu Ser Gln Ile Val Asp Ile Asp Gly Ile Trp Ser Gly
                260                 265                 270
Thr Arg Asp Phe Val Ala Cys Asn His Leu Arg Ser Tyr Lys Tyr Tyr
        275                 280                 285
Leu Glu Ser Ile Leu Asn Pro Asp Gly Phe Ala Ala Tyr Pro Cys Ala
    290                 295                 300
Ser Tyr Arg Asp Phe Glu Ser Asn Lys Cys Phe Pro Cys Pro Asp Gln
305                 310                 315                 320
Gly Cys Pro Gln Met Gly His Tyr Ala Asp Lys Phe Ala Asn Asn Thr
                325                 330                 335
Ser Val Glu Pro Gln Lys Phe Phe Leu Asn Thr Gly Glu Ala Lys Asn
            340                 345                 350
Phe Ala Arg Trp Arg Tyr Arg Val Ser Leu Thr Phe Ser Gly Arg Thr
        355                 360                 365
Val Thr Gly Gln Val Lys Val Ser Leu Phe Gly Ser Asn Gly Asn Thr
    370                 375                 380
Arg Gln Cys Asp Ile Phe Arg Gly Ile Ile Lys Pro Gly Ala Thr His
385                 390                 395                 400
Ser Asn Glu Phe Asp Ala Lys Leu Asp Val Gly Thr Ile Glu Lys Val
                405                 410                 415
Lys Phe Leu Trp Asn Asn His Val Val Asn Pro Ser Phe Pro Lys Val
            420                 425                 430
Gly Ala Ala Lys Ile Thr Val Gln Lys Gly Glu Glu Arg Thr Glu His
        435                 440                 445
Asn Phe Cys Ser Glu Glu Thr Val Arg Glu Asp Ile Leu Leu Thr Leu
    450                 455                 460
Leu Pro Cys Lys Thr Ser Asp Thr Met
465                 470

<210> SEQ ID NO 8
<211> LENGTH: 473
<212> TYPE: PRT
<213> ORGANISM: Rattus norvegicus

<400> SEQUENCE: 8

Met Leu Thr Leu Trp Thr Val Ser Leu Phe Leu Leu Gly Ala Ala Gln
1               5                   10                  15
Gly Lys Glu Val Cys Tyr Asp Asn Leu Gly Cys Phe Ser Asp Ala Glu
                20                  25                  30
Pro Trp Ala Gly Thr Ala Ile Arg Pro Leu Lys Leu Leu Pro Trp Ser
            35                  40                  45
Pro Glu Lys Ile Asn Thr Arg Phe Leu Leu Tyr Thr Asn Glu Asn Pro
        50                  55                  60
Thr Ala Phe Gln Thr Leu Gln Leu Ser Asp Pro Leu Thr Ile Gly Ala
65                  70                  75                  80
Ser Asn Phe Gln Val Ala Arg Lys Thr Arg Phe Ile Ile His Gly Phe
                85                  90                  95
```

```
Ile Asp Lys Gly Glu Glu Asn Trp Val Val Asp Met Cys Lys Asn Met
            100                 105                 110
Phe Gln Val Glu Glu Val Asn Cys Ile Cys Val Asp Trp Lys Lys Gly
            115                 120                 125
Ser Gln Thr Thr Tyr Thr Gln Ala Ala Asn Asn Val Arg Val Val Gly
            130                 135                 140
Ala Gln Val Ala Gln Met Ile Asp Ile Leu Val Lys Asn Tyr Ser Tyr
145                 150                 155                 160
Ser Pro Ser Lys Val His Leu Ile Gly His Ser Leu Gly Ala His Val
            165                 170                 175
Ala Gly Glu Ala Gly Ser Arg Thr Pro Gly Leu Gly Arg Ile Thr Gly
            180                 185                 190
Leu Asp Pro Val Glu Ala Asn Phe Glu Gly Thr Pro Glu Glu Val Arg
            195                 200                 205
Leu Asp Pro Ser Asp Ala Asp Phe Val Asp Val Ile His Thr Asp Ala
            210                 215                 220
Ala Pro Leu Ile Pro Phe Leu Gly Phe Gly Thr Asn Gln Met Ser Gly
225                 230                 235                 240
His Leu Asp Phe Phe Pro Asn Gly Gly Gln Ser Met Pro Gly Cys Lys
            245                 250                 255
Lys Asn Ala Leu Ser Gln Ile Val Asp Ile Asp Gly Ile Trp Ser Gly
            260                 265                 270
Thr Arg Asp Phe Val Ala Cys Asn His Leu Arg Ser Tyr Lys Tyr Tyr
            275                 280                 285
Leu Glu Ser Ile Leu Asn Pro Asp Gly Phe Ala Ala Tyr Pro Cys Ala
            290                 295                 300
Ser Tyr Lys Asp Phe Glu Ser Asn Lys Cys Phe Pro Cys Pro Asp Gln
305                 310                 315                 320
Gly Cys Pro Gln Met Gly His Tyr Ala Asp Lys Phe Ala Gly Lys Ser
            325                 330                 335
Gly Asp Glu Pro Gln Lys Phe Phe Leu Asn Thr Gly Glu Ala Lys Asn
            340                 345                 350
Phe Ala Arg Trp Arg Tyr Arg Val Ser Leu Ile Leu Ser Gly Arg Met
            355                 360                 365
Val Thr Gly Gln Val Lys Val Ala Leu Phe Gly Ser Lys Gly Asn Thr
            370                 375                 380
Arg Gln Tyr Asp Ile Phe Arg Gly Ile Ile Lys Pro Gly Ala Thr His
385                 390                 395                 400
Ser Ser Glu Phe Asp Ala Lys Leu Asp Val Gly Thr Ile Glu Lys Val
            405                 410                 415
Lys Phe Leu Trp Asn Asn Gln Val Ile Asn Pro Ser Phe Pro Lys Val
            420                 425                 430
Gly Ala Ala Lys Ile Thr Val Gln Lys Gly Glu Glu Arg Thr Glu Tyr
            435                 440                 445
Asn Phe Cys Ser Glu Glu Thr Val Arg Glu Asp Thr Leu Leu Thr Leu
            450                 455                 460
Leu Pro Cys Glu Thr Ser Asp Thr Val
465                 470
```

<210> SEQ ID NO 9
<211> LENGTH: 467
<212> TYPE: PRT
<213> ORGANISM: Canis familiaris -continued

```
<400> SEQUENCE: 9

Met Val Ser Ile Trp Thr Ile Ala Leu Phe Leu Leu Gly Ala Ala Lys
  1               5                  10                  15

Ala Lys Glu Val Cys Tyr Glu Gln Ile Gly Cys Phe Ser Asp Ala Glu
                 20                  25                  30

Pro Trp Ala Gly Thr Ala Ile Arg Pro Leu Lys Val Leu Pro Trp Ser
             35                  40                  45

Pro Glu Arg Ile Gly Thr Arg Phe Leu Leu Tyr Thr Asn Lys Asn Pro
         50                  55                  60

Asn Asn Phe Gln Thr Leu Leu Pro Ser Asp Pro Ser Thr Ile Glu Ala
 65                  70                  75                  80

Ser Asn Phe Gln Thr Asp Lys Lys Thr Arg Phe Thr Ile His Gly Phe
                 85                  90                  95

Ile Asn Lys Gly Glu Glu Asn Trp Leu Leu Asp Met Cys Lys Asn Met
            100                 105                 110

Phe Lys Val Glu Glu Val Asn Cys Ile Cys Val Asp Trp Lys Lys Gly
            115                 120                 125

Ser Gln Thr Ser Tyr Thr Gln Ala Ala Asn Val Arg Val Val Gly
130                 135                 140

Ala Gln Val Ala Gln Met Leu Ser Met Leu Ser Ala Asn Tyr Ser Tyr
145                 150                 155                 160

Ser Pro Ser Gln Val Gln Leu Ile Gly His Ser Leu Gly Ala His Val
                165                 170                 175

Ala Gly Glu Ala Gly Ser Arg Thr Pro Gly Leu Gly Arg Ile Thr Gly
            180                 185                 190

Leu Asp Pro Val Glu Ala Ser Phe Gln Gly Thr Pro Glu Glu Val Arg
            195                 200                 205

Leu Asp Pro Thr Asp Ala Asp Phe Val Asp Val Ile His Thr Asp Ala
            210                 215                 220

Ala Pro Leu Ile Pro Phe Leu Gly Phe Gly Thr Ser Gln Gln Met Gly
225                 230                 235                 240

His Leu Asp Phe Phe Pro Asn Gly Gly Glu Glu Met Pro Gly Cys Lys
                245                 250                 255

Lys Asn Ala Leu Ser Gln Ile Val Asn Leu Asp Gly Ile Trp Glu Gly
                260                 265                 270

Thr Arg Asp Phe Val Ala Cys Asn His Leu Arg Ser Tyr Lys Tyr Tyr
            275                 280                 285

Ser Glu Ser Ile Leu Asn Pro Asp Gly Phe Ala Ser Tyr Pro Cys Ala
290                 295                 300

Ser Tyr Arg Ala Phe Glu Ser Asn Lys Cys Phe Pro Cys Pro Asp Gln
305                 310                 315                 320

Gly Cys Pro Gln Met Gly His Tyr Ala Asp Lys Phe Ala Val Lys Thr
                325                 330                 335

Ser Asp Glu Thr Gln Lys Tyr Phe Leu Asn Thr Gly Asp Ser Ser Asn
            340                 345                 350

Phe Ala Arg Trp Arg Tyr Gly Val Ser Ile Thr Leu Ser Gly Lys Arg
            355                 360                 365

Ala Thr Gly Gln Ala Lys Val Ala Leu Phe Gly Ser Lys Gly Asn Thr
370                 375                 380

His Gln Phe Asn Ile Phe Lys Gly Ile Leu Lys Pro Gly Ser Thr His
385                 390                 395                 400

Ser Asn Glu Phe Asp Ala Lys Leu Asp Val Gly Thr Ile Glu Lys Val
                405                 410                 415
```

```
Lys Phe Leu Trp Asn Asn Asn Val Val Asn Pro Thr Phe Pro Lys Val
            420                 425                 430

Gly Ala Ala Lys Ile Thr Val Gln Lys Gly Glu Glu Lys Thr Val His
            435                 440                 445

Ser Phe Cys Ser Glu Ser Thr Val Arg Glu Asp Val Leu Leu Thr Leu
            450                 455                 460

Thr Pro Cys
465

<210> SEQ ID NO 10
<211> LENGTH: 467
<212> TYPE: PRT
<213> ORGANISM: Canis familiaris

<400> SEQUENCE: 10

Met Val Ser Ile Trp Thr Ile Ala Leu Phe Leu Leu Gly Ala Ala Lys
  1               5                  10                  15

Ala Lys Glu Val Cys Tyr Glu Gln Ile Gly Cys Phe Ser Asp Ala Glu
             20                  25                  30

Pro Trp Ala Gly Thr Ala Ile Arg Pro Leu Lys Val Leu Pro Trp Ser
         35                  40                  45

Pro Glu Arg Ile Gly Thr Arg Phe Leu Leu Tyr Thr Asn Lys Asn Pro
 50                  55                  60

Asn Asn Phe Gln Thr Leu Leu Pro Ser Asp Pro Ser Thr Ile Glu Ala
 65                  70                  75                  80

Ser Asn Phe Gln Thr Asp Lys Lys Thr Arg Phe Ile Ile His Gly Phe
             85                  90                  95

Ile Asp Lys Gly Glu Glu Asn Trp Leu Leu Asp Met Cys Lys Asn Met
            100                 105                 110

Phe Lys Val Glu Glu Val Asn Cys Ile Cys Val Asp Trp Lys Lys Gly
            115                 120                 125

Ser Gln Thr Ser Tyr Thr Gln Ala Ala Asn Asn Val Arg Val Val Gly
        130                 135                 140

Ala Gln Val Ala Gln Met Leu Ser Met Leu Ser Ala Asn Tyr Ser Tyr
145                 150                 155                 160

Ser Pro Ser Gln Val Gln Leu Ile Gly His Ser Leu Gly Ala His Val
            165                 170                 175

Ala Gly Glu Ala Gly Ser Arg Thr Pro Gly Leu Gly Arg Ile Thr Gly
            180                 185                 190

Leu Asp Pro Val Glu Ala Ser Phe Gln Gly Thr Pro Glu Glu Val Arg
            195                 200                 205

Leu Asp Pro Thr Asp Ala Asp Phe Val Asp Val Ile His Thr Asp Ala
        210                 215                 220

Ala Pro Leu Ile Pro Phe Leu Gly Phe Gly Thr Ser Gln Gln Met Gly
225                 230                 235                 240

His Leu Asp Phe Phe Pro Asn Gly Gly Glu Glu Met Pro Gly Cys Lys
            245                 250                 255

Lys Asn Ala Leu Ser Gln Ile Val Asp Leu Asp Gly Ile Trp Glu Gly
            260                 265                 270

Thr Arg Asp Phe Val Ala Cys Asn His Leu Arg Ser Tyr Lys Tyr Tyr
            275                 280                 285

Ser Glu Ser Ile Leu Asn Pro Asp Gly Phe Ala Ser Tyr Pro Cys Ala
        290                 295                 300

Ser Tyr Arg Ala Phe Glu Ser Asn Lys Cys Phe Pro Cys Pro Asp Gln
```

-continued

```
305                 310                 315                 320
Gly Cys Pro Gln Met Gly His Tyr Ala Asp Lys Phe Ala Val Lys Thr
                325                 330                 335
Ser Asp Glu Thr Gln Lys Tyr Phe Leu Asn Thr Gly Asp Ser Ser Asn
                340                 345                 350
Phe Ala Arg Trp Arg Tyr Gly Val Ser Ile Thr Leu Ser Gly Lys Arg
                355                 360                 365
Ala Thr Gly Gln Ala Lys Val Ala Leu Phe Gly Ser Lys Gly Asn Thr
            370                 375                 380
His Gln Phe Asn Ile Phe Lys Gly Ile Leu Lys Pro Gly Ser Thr His
385                 390                 395                 400
Ser Asn Glu Phe Asp Ala Lys Leu Asp Val Gly Thr Ile Glu Lys Val
                405                 410                 415
Lys Phe Leu Trp Asn Asn Asn Val Val Asn Pro Thr Phe Pro Lys Val
                420                 425                 430
Gly Ala Ala Lys Ile Thr Val Gln Lys Gly Glu Glu Lys Thr Val His
            435                 440                 445
Ser Phe Cys Ser Glu Ser Thr Val Arg Glu Asp Val Leu Leu Thr Leu
        450                 455                 460
Thr Pro Cys
465
```

HUMAN LIPASE PROTEINS, NUCLEIC ACIDS ENCODING THEM, AND USES OF BOTH OF THESE

BACKGROUND OF THE INVENTION

Lipids are esters of long chain fatty acids (generally $C_{14}$ to $C_{24}$ saturated and unsaturated fatty acids in animal fats) and polyols such as glycerol, glycerol phosphates, alkyl glyceryl ethers, glycerol phosphoryl-choline, glycerol phosphoryl-serine, glycerol phosphoryl-ethanolamine, and the like. Lipids, in the form of cell membranes and fats, for example, constitute a significant proportion of animal body weight (e.g., about 5% to 25% of body weight in normal humans).

Lipids are not water-soluble, and generally do not cross biological membranes efficiently by simple diffusion. Dietary lipids are taken up primarily by hydrolysis of fatty acyl moieties from their corresponding polyol moiety and diffusion of the two moieties across the gut wall (although limited uptake of intact lipids occurs). Following absorption, lipids are reformed by reestablishment of ester bonds between polyol and fatty acyl moieties, and lipids are delivered throughout the body in esterified form (generally in lipoprotein-containing particles such as chylomicrons, very low, intermediate, low, and high density lipoprotein particles, and the like). Prior to uptake by cells (either for storage or for metabolism), lipids must again be hydrolyzed in order to facilitate passage across the cell membrane. Thus, enzymes which catalyze formation and hydrolysis of the ester bonds between fatty acyl moieties and polyol moieties of lipids must be present at several physiological locations, and the particular activities catalyzed by these enzymes ('lipases') varies depending on the physiological location and function of the enzyme.

A number of lipase enzymes have been characterized in various organisms, including in humans. However, it is far from clear that all physiologically relevant lipases have been discovered or characterized. The present invention provides novel nucleotide and amino acid sequence information corresponding to one or more human lipases.

SUMMARY OF THE INVENTION

The present invention is based, at least in part, on discovery of human cDNA molecules which encode lipase proteins such as the one herein designated MLip-1. These proteins catalyze formation and cleavage of ester bonds between fatty acyl moieties and glyceride moieties. MLip-1 protein, fragments thereof, derivatives thereof, and variants thereof are collectively referred to herein as polypeptides of the invention or proteins of the invention. Nucleic acid molecules encoding polypeptides of the invention (i.e., nucleic acids encoding MLip-1 protein, fragments thereof, derivatives thereof, and variants thereof) are collectively referred to as nucleic acids of the invention.

The nucleic acids and polypeptides of the present invention are useful as modulating agents in regulating a variety of cellular processes, particularly including processes which involve lipid metabolism and pancreatic function. Accordingly, in one aspect, the present invention provides isolated nucleic acid molecules encoding a polypeptide of the invention or a biologically active portion thereof. The present invention also provides nucleic acid molecules which are suitable as primers or hybridization probes for detection of nucleic acids encoding a polypeptide of the invention.

The invention also includes nucleic acid molecules which are at least 40% (or, for example, 50%, 60%, 70%, 80%, 90%, 95%, or 98% or more) identical to the nucleotide sequence of either of SEQ ID NOs: 1 and 2, or a complement thereof.

The invention includes nucleic acid molecules which include a fragment of at least 56 (or, for example, 58, 60, 70, 80, 100, 125, 150, 200, 250, 300, 350, 400, 450, 550, 650, 700, 800, 900, 1000, 1200, 1400, 1600, 1800, 2000, or 2352) consecutive nucleotide residues of either of SEQ ID NOs: 1 and 2, or a complement thereof.

The invention also includes nucleic acid molecules which have a nucleotide sequence encoding a protein having an amino acid sequence that is at least 50% (or, for example, 60%, 70%, 80%, 90%, 95%, or 98% or more) identical to all or residues about 18–467 of the amino acid sequence SEQ ID NO: 3, or a complement thereof.

In certain embodiments, the nucleic acid molecules have the nucleotide sequence of either of SEQ ID NOs: 1 and 2.

Also within the invention are nucleic acid molecules which encode a fragment of a polypeptide having the amino acid sequence of SEQ ID NO: 3, the fragment including at least 17 (or, for example, 18, 20, 25, 30, 40, 50, 75, 100, 125, 150, 200, 250, 300, 400, or 467) consecutive amino acid residues of SEQ ID NO: 3.

The invention includes nucleic acid molecules which encode a naturally-occurring allelic variant of a polypeptide having the amino acid sequence of SEQ ID NO: 3, wherein the nucleic acid molecule hybridizes under stringent conditions with a nucleic acid molecule having a nucleic acid sequence comprising either of SEQ ID NOs: 1 and 2, or a complement thereof.

The invention also includes nucleic acid molecules that hybridize under stringent conditions with a nucleic acid molecule having the nucleotide sequence of either of SEQ ID NOs: 1 and 2, or a complement thereof. In other embodiments, the nucleic acid molecules are at least 56 (or, for example, 58, 60, 70, 80, 100, 125, 150, 200, 250, 300, 350, 400, 450, 550, 650, 700, 800, 900, 1000, 1200, 1400, 1600, 1800, 2000, or 2352) nucleotides in length and hybridize under stringent conditions with a nucleic acid molecule having the nucleotide sequence of either of SEQ ID NOs: 1 and 2, or a complement thereof. In some embodiments, the isolated nucleic acid molecules encode an immature or mature form of a polypeptide of the invention. In other embodiments, the invention provides an isolated nucleic acid molecule which is antisense with respect to the coding strand of a nucleic acid of the invention.

Another aspect of the invention provides vectors, e.g., recombinant expression vectors, comprising a nucleic acid molecule of the invention. In a related aspect, the invention provides isolated host cells, e.g., mammalian and non-mammalian cells, containing such a vector or a nucleic acid of the invention. The invention also provides methods for producing a polypeptide of the invention by culturing, in a suitable medium, a host cell of the invention containing a recombinant expression vector encoding a polypeptide of the invention such that the polypeptide of the invention is produced.

Another aspect of this invention includes isolated or recombinant proteins and polypeptides of the invention. Isolated polypeptides or proteins have an amino acid sequence that is at least about 50% (or, for example, 60%, 75%, 90%, 95%, or 98% or more) identical to all or a portion of the amino acid sequence of SEQ ID NO: 3. Exemplary polypeptides of the invention include a polypeptide having the amino acid sequence SEQ ID NO: 3, a polypeptide having the amino acid sequence of only residues 1 to about 17 of SEQ ID NO: 3 (i.e., the signal peptide of MLip-1), a polypeptide having the amino acid sequence of about residues 18 to 467 of SEQ ID NO: 3 (i.e., mature MLip-1 protein), and a polypeptide corresponding to a solvent-exposed portion of MLip-1 protein (e.g., about amino acid residues 80 to 105 of SEQ ID NO: 3).

Also within the invention are isolated polypeptides or proteins which are encoded by a nucleic acid molecule having a nucleotide sequence that is at least about 40% (or, for example, 50%, 75%, 85%, or 95% or more) identical to the nucleic acid sequence of either of SEQ ID NOs: 1 and 2, and isolated polypeptides or proteins which are encoded by a nucleic acid molecule having a nucleotide sequence which hybridizes under stringent hybridization conditions with a nucleic acid molecule having the nucleotide sequence of either of SEQ ID NOs: 1 and 2.

Also within the invention are polypeptides which are naturally-occurring allelic variants of a polypeptide that has the amino acid sequence SEQ ID NO: 3, wherein the polypeptide is encoded by a nucleic acid molecule which hybridizes under stringent conditions with a nucleic acid molecule having the nucleotide sequence of either of SEQ ID NOs: 1 and 2, or a complement thereof.

In certain embodiments, proteins and polypeptides possess at least one biological activity possessed by the corresponding naturally-occurring human polypeptide. An activity or a biological activity of a polypeptide of the invention refers to an activity exerted by the polypeptide of the invention on a responsive cell, on a portion of a cell (e.g., a cell membrane), on a cellular nutrient (e.g., a triglyceride or other lipid), or on a cellular metabolite or other product (e.g., cholesterol or membrane lipids). Such activity can be assessed in vivo or in vitro, according to standard techniques. MLip-1 polypeptides of the invention exhibit lipase activity, and can be involved in a number of bodily functions including, for example, dietary fat degradation and absorption, cholesterol biosynthesis, and maintenance of plasma lipid and lipoprotein levels. Such activities can, for example, be an enzymatic activity exerted by a polypeptide of the invention on another protein or on a non-protein substrate (e.g., on a lipoprotein particle or a triglyceride).

By way of example, protein MLip-1, compounds which modulate its activity, expression, or both, and compounds (e.g., antibodies) which bind with MLip-1 (collectively "MLip-1-related molecules") exhibit the ability to affect growth, proliferation, survival, differentiation, and activity of pancreatic tissue, in which MLip-1 is expressed. MLip-1-related molecules can be used to prevent, diagnose, or treat disorders relating to inappropriate lipid metabolism and aberrant pancreatic function. Exemplary disorders for which MLip-1-related molecules are useful include diabetes, obesity, nutritional disorders (e.g., lipid malabsorption and malnutrition), metabolic disorders (particularly including lipid metabolism anomalies such as hyperlipidemia of types I to V and hypolipidemia), pancreatitis, obstruction of the pancreatic duct, various lipidoses (e.g., Gaucher's disease and Niemann-Pick disease), atherosclerosis, arteriosclerosis, coronary artery disease, perforated peptic ulcer, abdominal lesions, intestinal obstruction, peritonitis, and other diseases and disorders associated with aberrant or physiologically inappropriate lipase and lipase-like activity.

In one embodiment, a polypeptide of the invention has an amino acid sequence that is sufficiently identical to an identified domain of MLip-1 (e.g., a domain present at the surface of MLip-1 or the lipase domain described herein) that the polypeptide exhibits an antigenic or enzymatic characteristic of MLip-1. Such polypeptides comprise at least about 17 (18, 20, 25, 35, 50, 75, 100, 150, 200, 250, or 300 or more) amino acid residues, of which at least about 65%, preferably at least about 75%, and more preferably at least about 85%, 95%, or 98% are identical or similar (representing conservative amino acid substitutions; i.e., between amino acids having similar side chain moieties). Exemplary antigenic and enzymatic characteristics of MLip-1 which are exhibited by such polypeptides include lipase activity, ability to bind with molecules (e.g., enzymatic substrates or cell-surface or lipoprotein particle surface sites) with which MLip-1 is able to bind, and ability to induce production of antibody substances (e.g., free and cell-surface-bound immunoglobulins such as antibodies and T cell receptors) which bind specifically with an epitope which occurs at or near the surface of MLip-1 protein.

The polypeptides of the present invention, or biologically active portions thereof, can be operably linked with a heterologous amino acid sequence to form fusion proteins. In addition, one or more polypeptides of the invention or biologically active portions thereof can be incorporated into pharmaceutical compositions, which can optionally include pharmaceutically acceptable carriers. Such pharmaceutical compositions can be used to treat or prevent one or more of the disorders identified herein.

The invention encompasses antibody substances that specifically bind with a polypeptide of the invention including, for example, MLip-1 protein and fragments thereof. Exemplary antibody substances that are included within the scope of the invention are monoclonal and polyclonal antibodies, antibody fragments, single-chain antibodies, free and cell-surface-bound antibodies, and T cell receptors. These antibody substances can be made, for example, by providing the polypeptide of the invention to an immunocompetent vertebrate and thereafter harvesting blood or serum from the vertebrate. Antibody substances can, alternatively, be generated by screening a library of phage (e.g., a filamentous phage such as M13) which express one or more immunoglobulin subunits (e.g., IgG heavy chains) on their surface to identify phage particles which display a subunit which binds with MLip-1 or an epitope thereof.

In another aspect, the present invention provides methods for detecting activity or expression of a polypeptide of the invention in a biological sample by contacting the biological sample with an agent capable of detecting such activity (e.g., a labeled substrate or another compound that can be detected after being acted upon by an active polypeptide of the invention), with an agent which binds specifically with a polypeptide of the invention (e.g., an antibody substance of the invention), or with an agent for detecting production of an RNA encoding a polypeptide of the invention (e.g., a reverse transcriptase primer complementary to a portion of an mRNA encoding the polypeptide).

The present invention also provides diagnostic assays for identifying the presence or absence of a genetic lesion or mutation characterized by at least one of: (i) aberrant modification or mutation of a gene encoding a polypeptide of the invention; (ii) mis-regulation of a gene encoding a polypeptide of the invention; and (iii) aberrant post-translational modification of a polypeptide of the invention wherein a wild-type form of the gene encodes a polypeptide which exhibits at least one activity of the polypeptide of the invention. Such diagnostic assays include, for example, (i) comparing the nucleotide sequence of all or part of a gene which encodes a polypeptide of the invention and which is obtained from a subject with the nucleotide sequence (or the corresponding part thereof) of a gene obtained from a subject having a non-mutated MLip-1 gene or one of SEQ ID NOs: 1 and 2; (ii) comparing the presence or level in a sample obtained from a subject of a polypeptide or polynucleotide corresponding to all or part of MLip-1 with the presence or level in other samples (preferably samples of the same type) obtained from one or more other subjects; and (iii) determining whether a polypeptide or polynucleotide corresponding to all or a part of MLip-1 that includes a sequence corresponding to a post-translational modification site identified herein, or determining whether a polypeptide of the invention is modified at such a site.

In another aspect, the invention provides a method for identifying a compound that modulates (i.e., inhibits or enhances) the activity of or binds with a polypeptide of the invention. In general, such methods entail measuring a biological activity of the polypeptide in the presence and absence of a test compound and identifying those compounds which alter the activity of the polypeptide. Such methods can be performed in vitro or in vivo (e.g., in an animal which naturally expresses the polypeptide or nucleic acid or in an animal that has been modified such that it artificially expresses the polypeptide or nucleic acid).

The invention also includes methods of identifying a compound that modulates expression of a polypeptide or nucleic acid of the invention by measuring expression of the polypeptide or nucleic acid in the presence and absence of the compound.

In another aspect, the invention provides methods for modulating activity of a polypeptide of the invention, the methods comprising contacting a cell with an agent that modulates the activity or expression of the polypeptide, such that activity or expression in the cell is modulated (e.g., by contacting the cell with a sufficient amount of the agent). In one embodiment, the agent is an antibody that specifically binds with a polypeptide of the invention. In another embodiment, the agent modulates expression of a polypeptide of the invention by modulating transcription, splicing, or translation of an RNA (e.g., a pre-mRNA or an mRNA) encoding the polypeptide of the invention. In yet another embodiment, the agent is a nucleic acid molecule having a nucleotide sequence that is antisense with respect to the coding strand of an RNA encoding a polypeptide of the invention. In still other embodiments, the agent is a small molecule (e.g., a compound having a molecular weight less than about 5,000) which modulates activity or expression of a polypeptide or nucleic acid of the invention.

In yet another aspect, the invention includes a method of treating a patient afflicted with a disorder characterized by aberrant activity of a polypeptide of the invention, or by aberrant expression of a nucleic acid of the invention. The method comprises administering to the patient an agent (e.g., a nucleic acid, polypeptide, small molecule, antibody, or the like) in an amount effective to modulate the activity of the polypeptide in the patient or a to modulate the expression of the nucleic acid in the patient. Following administration of the agent, at least one symptom of the disorder is alleviated. In an alternative method of treating a patient afflicted with a disorder associated with aberrant activity or expression of MLip-1 protein, the method comprises administering to the patient, in an amount effective to modulate the level of activity of the protein in the patient, an agent selected from the group consisting of i) a polypeptide of the invention;
ii) a variant of a polypeptide of the invention;
iii) a nucleic acid encoding a polypeptide of the invention; and
iv) an antisense nucleic acid which is capable of annealing with either of an mRNA encoding a polypeptide of the invention and a portion of a genomic DNA encoding a polypeptide of the invention.

Following administration of the agent, at least one symptom of the disorder is alleviated.

In still another aspect, the invention relates to a method of diagnosing a disorder associated with aberrant expression of MLip-1 protein in a patient. This method comprises assessing the level of expression of the gene encoding the protein (e.g., by assessing the quantity of a corresponding RNA, the quantity of a corresponding protein, or the activity of a corresponding protein) in the patient and comparing the level of expression of the gene with the normal level of expression of the gene in a human not afflicted with the disorder. A difference between the level of expression of the gene in the patient and the normal level is an indication that the patient is afflicted with the disorder.

The invention also includes a method of diagnosing a disorder associated with expression of an aberrant or mutated MLip-1 protein in a patient. This method can be performed by comparing the nucleotide sequence of a nucleic acid encoding MLip-1 protein in a patient with a nucleotide sequence (e.g., one of SEQ ID NOs: 1 and 2) encoding MLip-1 protein in a subject not afflicted with the disorder. A difference between the two nucleotide sequences is an indication that the patient is afflicted with the disorder. This method can also be performed by comparing the amino acid sequence of a portion (i.e., including all) of MLip-1 protein in a sample obtained from the patient with the amino acid sequence of the same portion of MLip-1 protein in a sample obtained from a subject not afflicted with the disorder. A difference between the two amino acid sequences is an indication that the patient is afflicted with the disorder.

In yet another aspect, the invention relates to a method of determining whether a patient is likely to become afflicted in the future with a disorder associated with aberrant expression of MLip-1 protein or with expression of an aberrant or mutated MLip-1 protein. In various embodiments, these prognostic methods comprise (i) comparing the nucleotide sequence of a nucleic acid encoding MLip-1 protein in a sample obtained from a patient with a nucleotide sequence (e.g., one of SEQ ID NOs: 1 and 2) encoding MLip-1 protein in a subject known not to be afflicted; and not to be predisposed to becoming afflicted with the disorder or (ii) comparing the amino acid sequence of all or a portion of MLip-1 protein obtained from a patient with the amino acid sequence (e.g., SEQ ID NO: 3) of MLip-1 protein obtained from a non-afflicted subject.

Other features and advantages of the invention will be apparent from the following detailed description and claims.

BRIEF DESCRIPTION OF THE DRAWINGS

FIG. 1, comprising FIGS 1A and 1B, is an alignment of the amino acid sequences of MLip-1 (SEQ ID NO: 3), hPL (SEQ ID NO: 4; GenBank accession number M93283), hPLRP1 (SEQ ID NO: 5; GenBank accession number M93284), and hPLRP2 (SEQ ID NO: 6; GenBank accession number M93285) proteins made by the CLUSTAL method, using DNAStar-Megalign software (PAM250 residue weight table and default parameters).

FIG. 2 comprises FIGS. 2A, 2B, and 2C. The consensus nucleotide sequence (SEQ ID NO: 1) of a cDNA encoding the human MLip-1 protein described herein is listed in FIGS. 2A and 2B. The amino acid sequence (SEQ ID NO: 3) of human MLip-1 protein is listed in FIG. 2C.

FIGS. 3A–3C are alignments of the amino acid sequences of MLip-1 (SEQ ID NO: 3), *Mus musculus* pancreatic lipase related protein 1 (MPLRP1; SEQ ID NO: 7; GenBank accession number G13108175), *Rattus norvegicus* pancreatic lipase related protein 1 precursor (RPLRP1p; SEQ ID NO: 8; GenBank accession number SP P54316), *Canis familiaris* pancreatic triacylglycerol lipase precursor (CPTLP; SEQ ID NO: 9; GenBank accession number GI 164048), and *Canis familiaris* pancreatic lipase related protein 1 precursor (CPLRP1p; SEQ ID NO: 10; GenBank accession number SP P06857), the alignment made by the CLUSTAL method using DNAStar-Megalign software (PAM250 residue weight table and default parameters).

DETAILED DESCRIPTION OF THE INVENTION

Figure 4:
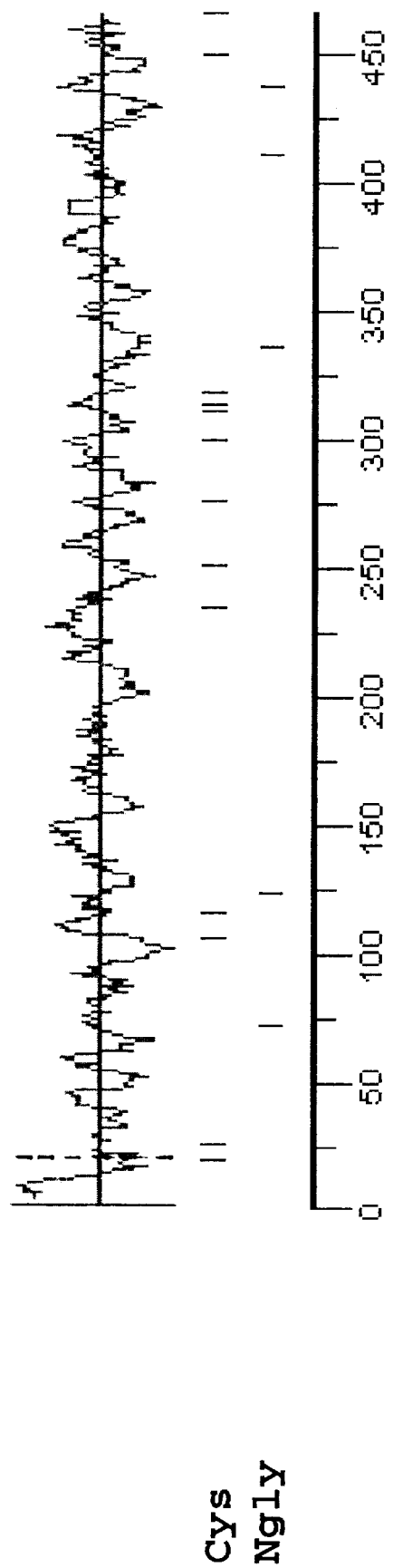
FIG. 4 is a hydrophilicity plot of human MLip-1 protein, in which the locations of cysteine residues ("Cys") and potential N-glycosylation sites ("Ngly") are indicated by vertical bars. Portions of the plot situated above the horizontal line correspond to hydrophobic regions of the protein, and portions of the plot situated below the horizontal line correspond to hydrophilic regions of the protein. The dashed vertical line indicates the approximate location of the signal sequence cleavage site.

The present invention is based, at least in part, on identification of a human cDNA molecule which encodes a protein herein designated MLip-1. MLip-1 is a lipase that is highly expressed in pancreatic tissue. The invention includes MLip-1 protein, fragments, derivatives, and variants thereof (individually and collectively, "polypeptides of the invention"), nucleic acids encoding polypeptides of the invention, compounds (e.g., antibodies and portions thereof and complementary polynucleotides) which bind with one or more polypeptides or nucleic acids of the invention, and compounds (e.g., small molecules) which modulate the activity, expression, or both, of one or more polypeptides or nucleic acids of the invention.

Certain characteristics of MLip-1 are now described.

Lipase MLip-1

A cDNA encoding at least a portion of human MLip-1 protein was identified. MLip-1 protein is predicted by structural analysis to be a secreted protein.

The full length of the cDNA encoding human MLip-1 (FIG. 2; SEQ ID NO: 1) is 2352 nucleotide residues. The ORF of this cDNA, nucleotide residues 125 to 1525 of SEQ ID NO: 1 (i.e., SEQ ID NO: 2), encodes a 467-amino acid residue immature protein (FIG. 2C; SEQ ID NO: 3) which exhibits amino acid sequence homology with a number of lipases and lipase-related proteins and which corresponds to an approximately 449-amino acid residue mature protein. As indicated in FIG. 4, the signal sequence of MLip-1 extends from amino acid residue 1 to about residue 17 of SEQ ID NO: 3. This cleavage site was predicted using the signal peptide prediction program SIGNALP (Nielsen et al. (1997) *Protein Engineering* 10:1–6). It is recognized that the carboxyl terminal boundary of the signal sequence predicted using this program can be located one or two residues from the residue identified above (i.e., from about residue 15 to 19 of SEQ ID NO: 3). The signal sequence is normally cleaved during processing of the mature protein, yielding secreted mature MLip-1. However, it is recognized that MLip-1 protein can persist, at least transiently, in a membrane-bound form in which the signal sequence has not been cleaved. Mature MLip-1 protein can be synthesized without the signal sequence polypeptide at the amino terminus thereof, or it can be synthesized by generating immature MLip-1 protein and cleaving the signal sequence therefrom.

MLip-1 proteins typically comprise a variety of potential post-translational modification sites, such as those described herein in Table I, as predicted by computerized sequence analysis of human MLip-1 protein using amino acid sequence comparison software (comparing the amino acid sequence of MLip-1 with the information in the PROSITE database {rel. 12.2; Feb, 1995} and the Hidden Markov Models database {Rel. PFAM 3.3}). In certain embodiments, a protein of the invention has at least 1, 2, 4, 6, 8, 10, or 15 or more of the post-translational modification sites listed in Table I.

TABLE I

| Type of Potential Modification Site or Domain | Amino Acid Residues of SEQ ID NO: 3 | Amino Acid Sequence |
|---|---|---|
| N-glycosylation site | 74 to 77 | NSST |
| | 125 to 128 | NGSR |
| | 338 to 341 | NGSH |
| | 412 to 415 | NITS |
| | 439 to 442 | NTSG |
| N-myristoylation site | 13 to 18 | GTSRGK |
| | 31 to 36 | GLPWTR |
| | 141 to 146 | GAEVAY |
| | 170 to 175 | GAHLAG |
| | 189 to 194 | GLDPAG |
| | 231 to 236 | GTIDAC |
| | 365 to 370 | GSEVTQ |
| | 378 to 383 | GGAIGK |
| | 397 to 402 | GMTYTK |
| | 411 to 416 | GNITSV |
| Lipase serine active site | 162 to 171 | VHLIGHSLGA |
| Lipase domain | 42 to 343 | See FIG. 2 |
| PLAT/LH2 domain | 355 TO 467 | See FIG. 2 |

MLip-1 protein comprises a lipase domain from about amino acid residue 42 to about residue 343, including a conserved (among lipases) active site serine residue at residue 168 of MLip-1. In one embodiment, the protein of the invention has at least one domain that is at least about 55%, preferably at least about 65%, more preferably at least about 75%, yet more preferably at least about 85%, and most preferably at least about 95% identical to this lipase domain. Proteins of the invention also have a serine residue at a position corresponding to serine-168 of MLip-1 although, of course, the residue number at which the serine residue occurs can vary, depending on the precise sequence of the protein. Lipase domains occur in a variety of proteins involved in formation and hydrolysis of one or more ester bonds of mono-, di-, and tri-glycerides. Such proteins include, for example, pancreatic lipases involved in dietary fat absorption, hepatic lipases involved in cholesterol biosynthesis, lipoprotein lipases involved in hydrolysis of lipids associated with chylomicrons and plasma lipoprotein particles (e.g., very low, intermediate, low, and high density lipoprotein particles), and gastric/lingual lipases involved in initial degradation of dietary fats.

The amino acid sequence of nearly all lipase active sites conforms to the following consensus sequence:

{L,I,or V}-X-{L,I,V,F,or Y}-{L,I,V,M,S,or T}-G-{H,Y,W,or V}-S*-X-G-{G,S,T,A,or C} wherein standard single amino acid codes are used (X being any amino acid residue). The serine residue marked with an asterisk is the active site residue. This consensus lipase serine active site sequence occurs in the amino acid sequence of MLip-1, as indicated in Table I.

Occurrence of a lipase domain, including a consensus lipase active site, in the amino acid sequence of MLip-1 indicates that MLip-1 is a lipase, or at least exhibits lipase or lipase-like activity. MLip-1 is thus able to catalyze formation and breakage of ester bonds that link one or more fatty acids to a glycerol moiety such as glycerol, glycerol phosphates, alkyl glyceryl ethers, glycerol phosphoryl-choline, glycerol phosphoryl-serine, glycerol phosphoryl-ethanolamine, sphingolipids, cerebrosides, and the like.

MLip-1 protein of the invention also contains a PLAT/LH2 domain (polycystin-1, lipoxygenase, alpha-toxin domain or lipoxygenase homology domain). PLAT/LH2 domains occur in a variety of membrane- and lipid-associated proteins, including many known lipases, and mediate association of protein with membranes and lipid vesicles (e.g., cell membranes and lipid globules that occur in the digestive tract and blood stream). Occurrence of a PLAT/LH2 domain in MLip-1 is thus a further indication that this protein exhibits lipase activity, particularly with regard to degradation of extracellular lipids and generation and interconversion of membrane-associated lipids.

MLip-1 protein exhibits amino acid sequence similarity to human pancreatic proteins hPL (human pancreatic lipase), HPLRP 1, and hPLRP2 (human pancreatic lipase related proteins 1 and 2, respectively; Giller et al., 1992, J. Biol. Chem. 267:16509–16516; GenBank accession Nos. M93283, M93284, and M93285, respectively), as indicated herein in FIGS. 1A and 1B. FIGS. 1A and 1B depict an alignment of the amino acid sequences of human protein MLip-1 (SEQ ID NO: 3) with the amino acid sequences of hPL (SEQ ID NO: 4), hPLRP1 (SEQ ID NO: 5), and hPLRP2 (SEQ ID NO: 6). In this alignment (PAM250 residue weight table), the amino acid sequence of MLip-1 is revealed to be about 48% identical to the amino acid sequence of hPL, about 47% identical to the amino acid sequence of HPLRP1, and about 46% identical to the amino acid sequence of hPLRP2.

As described in the prior art, hPL, hPLRP1, and hPLRP2 appear to be secreted proteins (Giller et al., 1992, J. Biol. Chem. 267:16509–16516). The sequence similarity of MLip-1 with hPL, hPLRP1, and hPLRP2 is a further indication that MLip-1 is a secreted protein. When MLip-1 is secreted from an exocrine portion of the pancreas, MLip-1 is able to catalyze conversion of dietary fats (i.e., mono-, di-, and tri-glycerides) into compounds (e.g., fatty acids, glycerol moieties, and the like) than are more readily absorbed by the body. When MLip-1 is secreted from a non-endocrine portion of pancreatic or other tissue, it is capable of catalyzing inter-conversion of fatty acids and mono-, di-, and tri-glycerides (i.e., including phosphatides, phosphatidyl cholines, phosphatidyl serines, phosphatidyl ethanolamines, and the like), thereby modulating lipid metabolism of cells of pancreatic tissue and tissues located in fluid communication with pancreatic tissue.

Protein MLip-1 also exhibits sequence similarity to several non-human lipase-related proteins, as indicated in FIGS. 3A through 3C. These figures depict an alignment of the amino acid sequences of human protein MLip-1 (SEQ ID NO: 3) with the amino acid sequences of *Mus musculus* pancreatic lipase related protein 1 (Remington et al., 1999, Invest. Ophthalmol. Vis. Sci. 40:1081–1090; GenBank accession number AF061274; SEQ ID NO: 7), *Rattus norvegicus* pancreatic lipase related protein 1 precursor (Wicker-Planquart et al., 1992, FEBS Lett. 296:61–66; GenBank accession number X61925; SEQ ID NO: 8), *Canis familiaris* pancreatic triacylglycerol lipase precursor (Kerfelec et al., 1986, Pancreas 1:430–437; GenBank accession number M35302; SEQ ID NO: 9), and *Canis familiaris* pancreatic lipase related protein 1 precursor (Mickel et al., 1989, J. Biol. Chem. 264:12895–12901; SwissProt accession number P06857; SEQ ID NO: 10). In this alignment (PAM250 residue weight table), the amino acid sequence of MLip-1 is revealed to be about 49% identical to SEQ ID NO: 7, about 49% identical to SEQ ID NO: 8, about 49% identical to SEQ ID NO: 9, and about 49% identical to SEQ ID NO: 10. Similarity of MLip-1 to these non-human lipase-related proteins is further evidence that MLip-1 exhibits lipase or lipase-like activity.

FIG. 4 depicts a hydrophilicity plot of protein MLip-1. Relatively hydrophobic regions are above the dashed horizontal line, and relatively hydrophilic regions are below the dashed horizontal line. As described elsewhere herein, relatively hydrophilic regions are generally located at or near the surface of a protein, and are more frequently effective immunogenic epitopes than are relatively hydrophobic regions. For example, the region of human protein MLip-1 from about amino acid residue 95 to about amino acid residue 105 appears to be located at or near the surface of the protein, while the region from about amino acid residue 135 to about amino acid residue 150 appears not to be located at or near the surface.

The predicted molecular weight of human protein MLip-1 is about 52 kilodaltons prior to cleavage of the predicted signal sequence, and about 50 kilodaltons after cleavage of the predicted signal sequence.

Northern blot analysis of human adult and fetal tissues indicated that mRNA corresponding to the cDNA encoding MLip-1 is expressed at detectable levels only in pancreas tissue.

Biological Function of Human MLip-1 Proteins, Nucleic Acids Encoding them, and Modulators of these Molecules The observation that MLip-1 protein is expressed in pancreatic tissue indicates that MLip-1 is a lipase involved in aberrant and normal nutritional uptake and metabolism of lipids. Thus, MLip-1 protein has a role in disorders which involve lipid uptake and metabolism.

Occurrence of a lipase domain in protein MLip-1 is a further indication that MLip-1 exhibits lipase activity and is involved in disorders relating to lipid uptake and metabolism. Such disorders include one or more of disorders which affect formation or hydrolysis of ester bonds between fatty acyl moieties and glycerol moieties (i.e., including glycerol, glycerol phosphates, alkyl glyceryl ethers, glycerol phosphoryl-choline, glycerol phosphoryl-serine, glycerol phosphoryl-ethanolamine, and the like), disorders which affect serum levels of lipid-containing particles (e.g., chylomicrons, lipoprotein particles, and the like), and disorders which affect transmembrane transport of fatty acids. Specific examples of such disorders include diabetes, obesity, hyperlipidemia, hypolipidemia, and various lipidoses.

The observation that human protein MLip-1 shares sequence homology with a number of other proteins involved in lipid metabolism (e.g., various pancreatic lipases and pancreatic lipase-related proteins) indicates that MLip-1 has activity identical or analogous to the activity of one or more of those proteins. Pancreatic lipases and lipase-related proteins are known to be involved in a variety of physiological processes including, for example, digestion of dietary lipids and normal pancreatic function. Aberrant expression or activity of MLip-1 is thus associated with lipid uptake disorders such as hyperlipidemia types I, II, III, IV, and V, hypolipidemia, obesity, various lipidoses (e.g., Gaucher's disease and Niemann-Pick disease), and linoleic acid deficiency, with pancreas-associated disorders such as pancreatitis, perforated peptic ulcer, abdominal lesions, intestinal obstruction, and peritonitis, with nutritional disorders such as lipid malabsorption and malnutrition, with atherosclerosis, with arteriosclerosis, and with coronary artery disease, for example.

Various aspects of the invention are described in further detail in the following subsections.

I. Isolated Nucleic Acid Molecules

In one aspect, the invention pertains to isolated nucleic acid molecules that encode a polypeptide of the invention or a biologically active portion thereof (e.g., mature human MLip-1), as well as nucleic acid molecules sufficient for use as hybridization probes to identify polynucleotides encoding a polypeptide of the invention and fragments of such nucleic acid molecules suitable for use as PCR primers for amplification or mutation (e.g., by site-directed mutagenesis) of polynucleotides. As used herein, the term "nucleic acid molecule" is intended to include DNA molecules (e.g., synthetic DNA, cDNA, or genomic DNA) and RNA molecules (e.g., pre-mRNA and mRNA) and analogs of the DNA or RNA generated using nucleotide analogs. The nucleic acid molecule can be single-stranded or double-stranded.

An "isolated" nucleic acid molecule is one which is separated from other nucleic acid molecules which are present in the natural source of the nucleic acid molecule. An isolated nucleic acid molecule can be free or substantially free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5, 4, 3, 2, 1, 0.5, or 0.1 kilobase pairs of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of all or a portion of SEQ ID NOs: 1 and 2, or a complement thereof, or a nucleic acid which has a nucleotide sequence comprising one of these sequences, can be isolated using standard molecular biology techniques and the sequence information provided herein. Using all or a portion of the nucleic acid sequences of SEQ ID NO: 1 or 2 as a hybridization probe, nucleic acid molecules of the invention can be isolated using standard hybridization and cloning techniques (e.g., as described in Sambrook et al., Eds., *Molecular Cloning: A Laboratory Manual, 2nd ed., Cold Spring Harbor Laboratory*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another embodiment, an isolated nucleic acid molecule of the invention comprises a nucleic acid molecule which is a complement of the nucleotide sequence of SEQ ID NO: 1 or 2, or a portion thereof. A nucleic acid molecule which is complementary to a given nucleotide sequence is one which is sufficiently complementary to the given nucleotide sequence that it can hybridize to the given nucleotide sequence, thereby forming a stable duplex.

Moreover, nucleic acids of the invention can include a portion of a nucleic acid sequence encoding a full length polypeptide of the invention (i.e., MLip-1 protein). For example, the portion can be a fragment which can be used as a probe or primer for detecting or amplifying a portion of a nucleic acid that shares homology with or is complementary to a nucleic acid encoding MLip-1. Alternatively, the portion can be a fragment which encodes a biologically active portion of a polypeptide of the invention, including a fragment which can be transcribed, translated, or both, to yield an active polypeptide of the invention.

The nucleotide sequence determined from cloning of the MLip-1 gene enables generation of probes and primers designed for use in identifying and cloning homologs from other mammals. The probe or primer typically comprises a substantially purified oligonucleotide. The oligonucleotide typically has at least one region that hybridizes under stringent conditions to at least about 15, preferably about 25, more preferably about 50, 56, 58, 60, 70, 80, 100, 125, 150, 175, 200, 250, 300, 350, or 400 or more consecutive nucleotides of the sense or anti-sense sequence of a nucleic acid having the nucleic acid sequence of SEQ ID NO: 1 or 2, or of a naturally-occurring mutant or variant of one of SEQ ID NOs: 1 and 2.

Probes based on the sequence of a nucleic acid molecule of the invention can be used to detect transcripts or genomic sequences encoding the same protein molecule encoded by a selected nucleic acid molecule. The probe has a label attached thereto (e.g., a radioisotope, a fluorescent compound, an enzyme, or an enzyme co-factor). One or more such probes can be used as part of a diagnostic test kit for identifying cells or tissues which mis-express the protein, such as a kit for measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of one of SEQ ID NOs: 1 and 2, expressing the encoded portion of the polypeptide (e.g., by recombinant expression in vitro), and assessing the activity of the encoded portion of the polypeptide. If the encoded portion exhibits lipase or lipase-like activity, then the fragment encodes a biologically active portion of a polypeptide of the invention.

The invention further encompasses nucleic acid molecules that differ from the nucleotide sequence of SEQ ID NOs: 1 and 2 due to degeneracy of the genetic code and thus encode the same protein as that encoded by the nucleotide sequence of SEQ ID NO: 2.

In addition to the nucleotide sequences of SEQ ID NO: 2, it will be appreciated by those skilled in the art that DNA sequence polymorphisms that lead to changes in the amino acid sequence can exist within a population (e.g., the human population or particular groups, such as ethnic groups, within the human population). Such genetic polymorphisms can exist among individuals within a population due to natural allelic variation. An allele is one of a group of genes which occur alternatively at a given genetic locus.

As used herein, the phrase "allelic variant" refers to a nucleotide sequence which occurs at a given locus or to a polypeptide encoded by the nucleotide sequence. Such natural allelic variations can typically result in from 0.1% to about 5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

As used herein, the terms "gene" and "recombinant gene" refer to nucleic acid molecules comprising an open reading frame encoding a polypeptide of the invention.

Moreover, nucleic acid molecules encoding proteins of the invention from other species (i.e., homologs), which have a nucleotide sequence which differs from that of the human MLip-1 protein described herein are included within the scope of the invention. Nucleic acid molecules corresponding to natural allelic variants and homologs of a cDNA of the invention can be isolated based on their identity to human nucleic acid molecules using MLip-1 cDNA, or a portion thereof, as a hybridization probe according to standard hybridization techniques under stringent hybridization conditions. For example, a cDNA encoding one allelic variant of a protein of the invention can be isolated based on its hybridization with a nucleic acid molecule encoding a second allelic variant of the protein.

Accordingly, in another embodiment, an isolated nucleic acid molecule of the invention is at least 56 (or, for example, 58, 60, 70, 80, 100, 125, 150, 200, 250, 300, 350, 400, 450, 550, 650, 700, 800, 900, 1000, 1200, 1400, 1600, 1800, 2000, or 2352) nucleotides in length and hybridizes under stringent conditions with the nucleic acid molecule comprising the nucleotide sequence, preferably the coding sequence, of SEQ ID NO: 1 or 2, or a complement thereof. As used herein, the term "hybridizes under stringent conditions" is intended to describe conditions for hybridization and washing under which nucleotide sequences that are at least 60% (65%, 70%, 75%, 80%, 85%, 90%, preferably 95% or more) identical to each other typically remain hybridized to each other. Such stringent conditions are known to those skilled in the art and can be found in, for example, Current *Protocols in Molecular Biology*, John Wiley & Sons, N.Y. (1989), 6.3.1–6.3.6. A preferred, non-limiting example of stringent hybridization conditions is hybridization in 6x sodium chloride/sodium citrate (SSC) at about 45° C., followed by one or more washes in 0.2xSSC, 0.1% SDS at a temperature of from about 50° C. to 65° C. Preferably, an isolated nucleic acid molecule of the invention that hybridizes under stringent conditions to the sequence of one of SEQ ID NOs: 1 and 2, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., percent identity is equal to the number of identical positions divided by the total number of positions (e.g., overlapping positions) multiplied by 100). In one embodiment, the two sequences are the same length, at least after introducing gaps into one or both sequences.

Determination of percent identity between two sequences can be accomplished using any of a number of mathematical algorithm. A preferred, non-limiting example of a mathematical algorithm used for comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous with a nucleic acid molecule of the invention. BLAST protein searches can be performed using the XBLAST program, score=50, wordlength=3 to obtain amino acid sequences homologous to a protein molecules of the invention. To obtain gapped alignments for comparison purposes, gapped BLAST analysis can be used as described in Altschul et al. (1997) *Nucleic Acids Res.* 25:3389–3402. Alternatively, PSI-Blast can be used to perform an iterated search which detects distant relationships between molecules. Id. When using BLAST, gapped BLAST, and PSI-Blast analyses, default parameters of the respective programs (e.g., XBLAST and NBLAST) can be used. See http://www.ncbi.nlm.nih.gov. Another preferred, non-limiting example of a mathematical algorithm used for comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444–2448. When using the FASTA algorithm for comparing nucleotide or amino acid sequences, a PAM 120 weight residue table can, for example, be used with a κ-tuple value of 2.

The percent identity between two sequences can be determined using techniques similar to those described above, with or without allowing gaps. In calculating percent identity, only exact matches are counted.

In addition to naturally-occurring allelic sequence variants of a nucleic acid molecule of the invention that can exist in the population, the skilled artisan will further appreciate that changes can be introduced by mutation, thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity of MLip-1, whereas an "essential" amino acid residue is required for biological activity. For example, amino acid residues that are not conserved or are only semi-conserved among homologs of various species can be non-essential for activity and thus are likely targets for alteration. Alternatively, amino acid residues that are conserved among the homologs of various species (e.g., murine and human) can be essential for activity and thus are not likely targets for alteration.

Accordingly, another aspect of the invention pertains to nucleic acid molecules encoding a polypeptide of the invention that contain changes which alter amino acid residues that are not essential for activity. Such polypeptides differ in amino acid sequence from SEQ ID NO: 3, and yet retain biological activity. In one embodiment, the isolated nucleic acid molecule has a nucleotide sequence encoding a protein that includes an amino acid sequence that is at least about 40% identical (or, for example, 50%, 60%, 70%, 80%, 90%, 95%, or 98% identical) to the amino acid sequence of SEQ ID NO: 3.

An isolated nucleic acid molecule encoding a variant protein can be created by introducing one or more nucleotide substitutions, additions, or deletions into the nucleotide sequence of SEQ ID NO: 1 or 2, such that one or more amino acid residue substitutions, additions, or deletions are introduced into the encoded protein. Mutations can be introduced using standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), non-charged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recornbinantly and the activity of the protein can be determined.

The present invention encompasses antisense nucleic acid molecules, i.e., molecules which are complementary to a sense nucleic acid encoding a polypeptide of the invention or a portion thereof, such as nucleic acids complementary to the coding strand of a double-stranded cDNA molecule or complementary to an mRNA sequence. Accordingly, an antisense nucleic acid can hybridize with a sense nucleic acid. The antisense nucleic acid can be complementary to an entire coding strand, or to only a portion thereof, e.g., all or part of the protein coding region (or open reading frame). An antisense nucleic acid molecule can be antisense with respect to all or part of a non-coding region of the coding strand of a nucleotide sequence encoding a polypeptide of the invention. The non-coding regions ("5' and 3' non-translated regions") are the 5' and 3' sequences which flank the coding region and which are not normally translated into amino acids.

An antisense oligonucleotide can be, for example, about 10, 15, 20, 25, 30, 35, 40, 45, 50, 60 or more nucleotides in length. An antisense nucleic acid of the invention can be constructed using chemical synthetic or enzymatic ligation methods known in the art. For example, an antisense nucleic acid can be chemically synthesized using naturally-occurring nucleotides or variously modified nucleotides designed to increase the biological stability of the molecules or to increase the physical stability of the duplex formed between the antisense and sense nucleic acids. Examples of such modified nucleotides are phosphorothioate derivatives and acridine-substituted nucleotides. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylamino-methyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will have an antisense orientation with respect to a target nucleic acid of interest).

The antisense nucleic acid molecules of the invention are typically administered to a subject or generated in situ such that they hybridize with or bind with one or both of cellular mRNA and genomic DNA encoding a selected polypeptide of the invention. Hybridization of the antisense nucleic acid with the mRNA or genomic DNA inhibits expression of the protein by inhibiting translation or transcription, respectively. The hybridization can occur by means of conventional nucleotide complementarity to form a stable duplex, or, for example, in the case of an antisense nucleic acid molecule which binds with DNA duplexes, by means of specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind with receptors or antigens expressed on a selected cell surface, e.g., by linking the antisense nucleic acid molecules to peptides or antibodies which bind with cell surface receptors or antigens. The antisense nucleic acid molecules can also be delivered to cells using vectors described herein or other vectors. To achieve sufficient intracellular concentrations of the antisense molecules, vector constructs in which transcription of the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res.* 15:6625–6641). The antisense nucleic acid molecule can also comprise a 2'-o- methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules having ribonuclease activity. Ribdzymes are capable of cleaving a single-stranded nucleic acid, such as an mRNA, which has a portion to which a portion of the ribozyme is complementary. Thus, ribozymes (e.g., hammerhead ribozymes as described in Haselhoff and Gerlach (1988) *Nature* 334:585–591) can be used and catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site of this ribozyme is complementary to the portion of the mRNA to be cleaved, as described in U.S. Pat. No. 4,987,071 and U.S. Pat. No. 5,116,742. Alternatively, an mRNA encoding a polypeptide of the invention can be used to select, from a pool of RNA molecules, a catalytic RNA having a specific ribonuclease activity. See, e.g., Bartel and Szostak (1993) *Science* 261:1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter or enhancer region of a gene) to form triple helical structures that prevent transcription of the gene in target cells. See generally Helene (1991) *Anticancer Drug Des.* 6(6):569–84; Helene (1992) *Ann. N.Y. Acad. Sci.* 660:27–36; and Maher (1992) *Bioassays* 14(12):807–15.

In various embodiments, the nucleic acid molecules of the invention can be modified at the base moiety, sugar moiety, or phosphate backbone to improve, e.g., stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to enable specific hybridization between the PNA and DNA or RNA under conditions of low ionic strength. Synthesis of PNA oligomers can be performed using standard solid phase peptide synthesis protocols, as described (Hyrup et al. (1996), supra; Perry-O'Keefe et al. (1996) *Proc. Natl. Acad. Sci. USA* 93: 14670–675).

PNAs can be used in therapeutic and diagnostic applications. For example, PNAs can be used as antisense or antigene agents for sequence-specific modulation of gene expression by, e.g., by inducing transcription or translation arrest or by inhibiting replication. PNAs can also be used, e.g., for analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670–675).

In another embodiment, PNAs can be modified to enhance, for example, their stability or cellular uptake by attaching lipophilic or other helper groups to PNA, by formation of PNA-DNA chimeras, or using liposomes or other drug delivery compositions known in the art. For example, PNA-DNA chimeras can be generated which combine the advantageous properties of PNA and DNA. Such chimeras allow DNA recognition enzymes, e.g., RNASE H and DNA polymerases, to interact with the DNA portion, while the PNA portion provides high binding affinity and specificity. PNA-DNA chimeras can be made using linkers of appropriate lengths, selected in terms of base stacking, number of bonds between the nucleobases, and orientation, as described (Hyrup (1996), supra). PNA-DNA chimeras can be synthesized as described in Hyrup (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a step-wise manner to produce a chimeric molecule with a 5' PNA segment and a 3' DNA segment (Finn et al. (1996) *Nucleic Acids Res.* 24(17):3357–63). Alternatively, chimeric molecules can be synthesized which have a 5' DNA segment and a 3' PNA segment, as described (Peterser et al. (1 975) *Bioorganic Med. Chem. Lett.* 5:1119–11124).

In other embodiments, the oligonucleotide can include other appended groups such as peptides (e.g., for targeting host cell receptors in vivo), or agents which facilitate transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication number WO 88/09810) or the blood-brain barrier (see, e.g., PCT Publication number WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide can be conjugated to another molecule, e.g., a peptide, hybridization triggered cross-linking agent, transport agent, hybridization-triggered cleavage agent, etc.

II. Isolated Proteins

In another aspect, the invention pertains to isolated proteins, and biologically active portions thereof, as well as polypeptide fragments suitable for use as immunogens to generate antibodies which bind specifically with a polypeptide of the invention. In one embodiment, the native polypeptide is isolated from cells or tissue sources by an appropriate purification scheme using standard protein purification techniques. In another embodiment, polypeptides of the invention are produced by recombinant DNA techniques. As an alternative to recombinant expression, a polypeptide of the invention can be synthesized chemically using standard peptide synthesis techniques.

An "isolated" or "purified" protein or biologically active portion thereof is substantially free of cellular material or other contaminating proteins which originate in the cell or tissue source from which the protein is derived, or substantially free of chemical precursors or other chemicals, when the polypeptide of the invention is chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30% (or, for example, 20%, 10%, or 5%), by dry weight, heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30% (or, for example, 20%, 10%, 5%), by dry weight, chemical precursors or compounds other than the polypeptide of interest.

Biologically active portions of a polypeptide of the invention include polypeptides which have an amino acid sequence sufficiently identical to or derived from the amino acid sequence of MLip-1 protein (e.g., the amino acid sequence of SEQ ID NO: 3), which include fewer amino acids than the full length protein, and which exhibit at least one activity of the corresponding full-length protein. Typically, biologically active portions comprise a domain or motif which exhibits at least one activity (e.g., specific binding capacity or catalytic capacity) of the corresponding protein. A biologically active portion of a protein of the invention can be a polypeptide which is, for example, 10, 17, 18, 25, 50, 100, 150, 200, or 300 or more amino acid residues in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence SEQ ID NO: 3. Other useful proteins have an amino acid sequence which is substantially identical (e.g., at least about 40% or, for example, 50%, 60%, 70%, 80%, 90%, 95%, or 99%, identical) to SEQ ID NO: 3 and retain at least one activity of the corresponding naturally-occurring protein, yet differ in amino acid sequence due to natural allelic variation or mutagenesis.

In one embodiment, the invention includes a mutant polypeptide that is a variant of a polypeptide of the invention and can be assayed for: (1) the ability to form protein:protein interactions with the polypeptide of the invention; (2) the ability to bind a ligand of the polypeptide of the invention (e.g., a triglyceride or other lipid); (3) the ability to catalyze a chemical reaction (e.g. formation or breakage of acyl/glyceride bonds) by which a protein of the invention is characterized (e.g. lipase or lipase-like activity); or (4) the ability to modulate a physiological activity of the protein, such as one of those disclosed herein. Mutant polypeptides which exhibit one or more of these activities are included in the invention, as are methods of screening libraries of mutant polypeptides in order to identify ones which exhibit such activities.

The invention also provides chimeric or fusion proteins. As used herein, a "chimeric protein" or "fusion protein" comprises all or part (preferably a biologically active part) of a polypeptide of the invention operably linked with a heterologous polypeptide (i.e., a polypeptide other than the same polypeptide of the invention). Within the fusion protein, the term "operably linked" is intended to indicate that the polypeptide of the invention and the heterologous polypeptide are fused in-frame with each other. The heterologous polypeptide can be fused with the amino-terminus or the carboxyl-terminus of a polypeptide of the invention. Often, in fusion expression vectors, a proteolytic cleavage site is introduced at the junction of the two protein moieties to enable separation of the recombinant protein from the fusion moiety subsequent to purification of the fusion protein. Such enzymes, and their cognate recognition sequences, include Factor Xa, thrombin, and enterokinase.

One useful fusion protein is a GST fusion protein in which a polypeptide of the invention is fused with the carboxyl terminus of a GST sequence. Such fusion proteins can facilitate the purification of a recombinant polypeptide of the invention.

In another embodiment, the fusion protein contains a heterologous signal sequence at its amino terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992) in place of amino acid residues 1 to about 17 of SEQ ID NO: 3. Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused with sequences derived from a member of the immunoglobulin protein family. The immunoglobulin fusion proteins of the invention can be incorporated into pharmaceutical compositions and administered to a subject to inhibit an interaction between a ligand (e.g., a soluble or membrane-bound ligand) and a protein on the surface of a cell (e.g., a receptor), to thereby suppress signal transduction in vivo. Inhibition of ligand/receptor interaction can be useful therapeutically, for example for treating pancreas-related disorders and for modulating (e.g., promoting or inhibiting) lipid metabolism. Moreover, an immunoglobulin fusion protein of the invention can be used as an immunogen to produce antibodies directed against a polypeptide of the invention in a subject, to purify a ligand of a polypeptide of the invention, and in screening assays to identify a molecule which inhibits interaction of a polypeptide of the invention with a ligand thereof.

Chimeric and fusion proteins of the invention can be produced using standard recombinant DNA techniques. In another embodiment, the fission gene can be synthesized using conventional techniques including techniques which involve operation of an automated DNA synthesizer. Alternatively, PCR amplification of gene fragments can be performed using anchor primers which give rise to complementary overhanging regions at the end of consecutive gene fragments, which can subsequently be annealed and re-amplified to generate a chimeric gene sequence (see, e.g., Ausubel et al., supra). Moreover, many expression vectors are commercially available that encode a fusion protein moiety (e.g., a portion of a GST protein). Through exercise of ordinary skill, a nucleic acid encoding a polypeptide of the invention can be cloned into such an expression vector in such a way that the fusion moiety is linked in-frame with a polypeptide of the invention.

The present invention includes to variants of the polypeptides of the invention. Exemplary variants have an altered amino acid sequence and can function as either agonists (i.e., mimetics) or as antagonists of MLip-1. Variants can be generated by mutagenesis, e.g., discrete point mutation or truncation. An agonist can retain substantially the same, or a subset, of the biological activities associated with the naturally-occurring form of the protein. An antagonist of a protein can inhibit one or more of the activities of the naturally-occurring form of the protein by, for example, competitively binding a triglyceride and inhibiting transmembrane transport thereof. Thus, specific biological effects can be elicited by treatment with a variant of limited function. Treatment of a subject with a variant having a subset of the biological activities of the naturally-occurring form of the protein can have fewer side effects in a subject, relative to treatment with the naturally-occurring form of the protein.

Variants of a protein of the invention which function as either agonists (mimetics) or as antagonists can be identified by screening combinatorial libraries of mutants, e.g., truncation mutants, of MLip-1 for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et at. (1984) *Annu. Rev. Biochem.* 53:323; Itakura et at. (1984) *Science* 198:1056; Ike et al. (1983) *Nucleic Acid Res.* 11:477). Methods for assessing transmembrane transport of compounds such as triglycerides are known in the art.

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, re-naturing the DNA to form double stranded DNA which can include sense/antisense pairs from different nicked products, removing single stranded portions from reformed duplexes by treatment with SI nuclease, and ligating the resulting fragment library into an expression vector. Using this method, an expression library can be derived which encodes amino terminal and internal fragments of various sizes of MLip-1.

Several techniques are known in the art for screening gene products of combinatorial libraries made by point mutations or truncation, and for screening cDNA libraries for gene products having a selected property. The most widely used techniques (which are amenable to high throughput analysis) for screening large gene libraries typically include cloning the library into replicable expression vectors, transforming appropriate cells with the resulting library of vectors, and expressing the combinatorial genes under conditions in which detection of a desired activity facilitates isolation of the vector encoding the gene, the product of which was detected. Recursive ensemble mutagenesis (REM), a technique which enhances the frequency of functional mutants in the libraries, can be used in combination with one or more of the screening assays described herein to identify variants of MLip-1 (Arkin and Yourvan (1992) *Proc. Natl. Acad. Sci. USA* 89:7811–7815; Delgrave et al. (1 993) *Protein Engineering* 6(3):327–331).

III. Antibodies

An isolated polypeptide of the invention, or a fragment thereof, can be used as an immunogen to generate antibodies and other antibody substances using standard techniques for polyclonal and monoclonal antibody preparation. Full-length MLip-1 can be used or, alternatively, the invention provides antigenic peptide fragments for use as immunogens. The antigenic peptide of a protein of the invention comprises at least 8 (preferably 10, 15, 17, 18, 20, or 30 or more) amino acid residues of a protein having the amino acid sequence SEQ ID NO: 3 at those residues, and encompasses an epitope of the protein such that an antibody substance raised against the peptide (i.e., a polypeptide which binds specifically with the peptide) forms a specific immune complex with the protein.

Preferred epitopes encompassed by the antigenic peptide are regions that are located on the surface of the protein, e.g., hydrophilic regions. FIG. 4 is a hydrophobicity plot of MLip-1 protein. This plot or similar analyses (including a variety of known computer-based algorithms for analyzing protein sequence hydrophilicity/hydrophobicity) can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete adjuvant, Freund's incomplete adjuvant, or a similar immunostimulatory agent.

Accordingly, in one aspect, the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds with a polypeptide of the invention is a molecule which binds the polypeptide, but does not substantially bind other molecules in a sample, e.g., a biological sample which naturally contains the polypeptide. Examples of immunologically active portions of immunoglobulin molecules include F(ab) and F(ab')$_2$ fragments which can be generated by treating the antibody with an enzyme such as pepsin. The invention thus includes, for example, T cell receptors and polyclonal and monoclonal antibodies which bind specifically with MLip-1 protein or a fragment or variant thereof. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above, by immunizing a suitable subject with a polypeptide of the invention as an immunogen. The antibody titer in the immunized subject can be monitored over time by standard techniques, such as using an enzyme linked immunosorbent assay (ELISA) involving an immobilized polypeptide. If desired, the antibody molecules can be harvested or isolated from the subject (e.g., from the blood or serum of the subject) and further purified by well-known techniques, such as protein A chromatography to obtain the IgG fraction. At an appropriate time following inmunuization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77–96), or one of several known trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

As an alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharnacia Recombinant Phage Antibody System, Catalog number 27-9400-01; and the Stratagene SurfZAP Phage Display Kit, Catalog number 240612). Additionally, examples of methods and reagents particularly amenable for use in generating and screening antibody display library can be found in, for example, U.S. Pat. No. 5,223,409; PCT Publication number WO 92/18619; PCT Publication number WO 91/172721; PCT Publication number WO 92/20791; PCT Publication number WO 92/15679; PCT Publication number WO 93/01288; PCT Publication number WO 92/01047; PCT Publication number WO 92/09690; PCT Publication number WO 90/02809; Fuchs et al. (1991) *Bio/Technology* 9:1370–1372; Hay et al.;(1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication number WO 87/02671; European Patent Application 184,187; European Patent Application 171,496; European Patent Application 173,494; PCT Publication number WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liuetal. (1987)*J. Immunol.* 139:3521–3526; Sun et al. (1987) *Proc. Natl. Acad. Sci. USA* 84:214–218; Nishimura et al. (1987) *Cancer Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of MLip-1 protein. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique designated as "guided selection." In this approach, a selected non-human monoclonal antibody, e.g., a murine antibody, is used to guide selection of a completely human antibody recognizing the same epitope (Jespers et al. (1994) *Bio/technology* 12:899–903).

An antibody which binds specifically with a polypeptide of the invention (e.g., a monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to determine the efficacy of a given treatment regimen. Detection can be facilitated by coupling the antibody with a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride and phycoerythrin. An example of a luminescent material includes luminol. Examples of bioluminescent materials include luciferase, luciferin, green fluorescent protein, and aequorin. Examples of suitable radioactive material include $^{125}$I, $^{131}$I, $^{35}$S and $^{3}$H.

IV. Recombinant Expression Vectors and Host Cells

In another aspect, the invention pertains to vectors, preferably expression vectors which comprise a nucleic acid encoding a polypeptide of the invention. As used herein, the term "vector" refers to a nucleic acid molecule capable of transporting another nucleic acid with which it has been linked. One type of vector is a "plasmid", which refers to a circular, double stranded DNA loop into which additional DNA segments can be ligated. Another type of vector is a virus vector, wherein additional DNA segments can be ligated into the viral genome. Certain vectors are capable of autonomous replication in a host cell into which they are introduced (e.g., some virus vectors, bacterial vectors having a bacterial origin of replication, and episomal mammalian vectors). Other vectors (e.g., other virus vectors and non-episomal mammalian vectors) are integrated into the genome of a host cell upon introduction into the host cell and are replicated along with the host genome. Moreover, certain vectors, namely expression vectors, are capable of directing expression of genes or protein-coding sequences with which they are operably linked. Expression vectors useful in recombinant DNA techniques are often in the form of plasmids. However, the invention includes such other forms of expression vectors as virus vectors (e.g., replication defective retroviruses, adenoviruses, and adeno-associated viruses) and linear DNA vectors, which serve analogous functions.

The recombinant expression vectors of the invention comprise a nucleic acid of the invention in a form suitable for expression of the nucleic acid in a host cell. This means that the recombinant expression vectors include one or more regulatory sequences operably linked with the nucleic acid sequence to be expressed. The choice of regulatory sequence can depend on the host cells to be used for expression. Within a recombinant expression vector, "operably linked" is intended to mean that the nucleotide sequence of interest is covalently bonded with the regulatory sequence(s) in a manner which allows expression of the nucleotide sequence (e.g., in an in vitro transcription/translation system or in a host cell). The term "regulatory sequence" includes promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Design of the expression vector can depend on such factors as the identity of the host cell to be transformed, the level of expression of protein that is desired, and the like. The expression vectors of the invention can be introduced into host cells to produce proteins or peptides encoded by nucleic acids, including fusion proteins or peptides, as described herein.

The recombinant expression vectors of the invention can be designed for expression of a polypeptide of the invention in prokaryotic (e.g., *E. coli*) or eukaryotic cells (e.g., insect cells {e.g., using a baculovirus expression:vector}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase. Suitable in vitro transcription/translation methods and kits are known in the art.

Expression of proteins in prokaryotes is most often performed in *E. coli* using vectors which contain constitutive or inducible promoters that direct expression of either fusion or non-fusion proteins.

Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, with the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Gene expression from the pTrc vector relies on host RNA polymerase transcription from a hybrid tip-lac fusion promoter. Gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage which harbors a T7 gn1 gene under the transcriptional control of a lacUV 5 promoter.

One strategy for maximizing recombinant protein expression in *E. coli* is to express the protein in a host bacterium that has an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be done using standard DNA synthesis techniques.

In another embodiment, the expression vector is a yeast expression vector. Examples of vectors for expression in yeast *S. cerevisiae* include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and pPicZ (Invitrogen Corp, San Diego, Calif.).

Alternatively, the expression vector can be a baculovirus expression vector. Baculovirus vectors which are useful for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39) of vectors.

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, control of expression vector functions can be mediated by viral regulatory elements. For example, commonly used promoters are derived from polyoma virus, adenovirus 2, cytomegalovirus, and simian virus 40. For other suitable expression systems for both prokaryotic and eukaryotic cells, see chapters 16 and 17 of Sambrook et al., supra.

In another embodiment, the recombinant mammalian expression vector is capable of directing expression of the nucleic acid preferentially in a particular cell type. The vector comprises a tissue-specific regulatory elements are used to express the nucleic acid). Tissue-specific regulatory element operably linked with the nucleic acid. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), including promoters of T cell receptors (Winoto and Baltimore (1989) *EMBO J.* 8:729–733) and immunoglobulins (Banedji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication number 264,166). Vectors which comprise a developmentally-regulated promoters are also included, for example the murine hox promoters (Kessel and Gruss (1990) *Science* 249:374–379) and the α-fetoprotein promoter (Campes and Tilghman (1989) *Genes Dev.* 3:537–546).

The invention also includes a recombinant expression vector comprising a DNA molecule of the invention cloned into an expression vector in an antisense orientation. That is, the DNA molecule is operably linked with a regulatory sequence in a manner that enables expression (by transcription of the DNA molecule) of an RNA molecule which is antisense with respect to an mRNA encoding a polypeptide of the invention. Regulatory sequences operably linked with a nucleic acid cloned in an antisense orientation can be selected which direct continuous expression of the antisense RNA molecule in a variety of cell types. For example, viral promoters, enhancers, regulatory sequences, and combinations of these can be selected which direct constitutive, tissue-specific or cell type-specific expression of antisense RNA. An antisense expression vector can be in the form of a recombinant plasmid, phagemid, or attenuated virus from which antisense nucleic acids are produced under the control of a high efficiency regulatory region. The activity of such a region can be determined by the cell type into which the vector is introduced. For a discussion of regulation of gene expression using antisense genes, see Weintraub et al. (*Reviews—Trends in Genetics*, Vol. 1(1) 1986).

In another aspect, the invention pertains to host cells into which a recombinant expression vector of the invention has been introduced. The terms "host cell" and "recombinant host cell" are used interchangeably herein. It is understood that such terms refer not only to particular subject cells, but to the progeny or potential progeny of such cells as well. Because certain modifications can occur;in succeeding generations, due to mutation or environmental influences for example, such progeny will not, in some instances, be identical to the parent cells, but are nevertheless included within the scope of the invention. The host cell can be any prokaryotic (e.g., *E. coli*) or eukaryotic cell (e.g., insect cells, yeast, or mammalian cells).

Vector DNA can be introduced into prokaryotic or eukaryotic cells using conventional transformation or transfection techniques. As used herein, the 30 terms "transformation" and "transfection" are intended to refer to a variety of art-recognized techniques for introducing a foreign nucleic acid into a host cell. Such methods include, for example, calcium phosphate or calcium chloride co-precipitation, DEAE-dextran-mediated transfection, lipofection, and electroporation. Suitable methods for transforming or transfecting host cells are described in Sambrook, et al. (supra), and other laboratory manuals.

For stable transfection of mammalian cells, it is known that as few as a small fraction of cells integrate foreign DNA into their genome, depending on, for example, the identity of the cells and the expression vector and transfection technique used. In order to identify and select these integrants, a gene that encodes a selectable marker (e.g., an antibiotic resistance marker) can be introduced into the host cells along with the gene of interest. Preferred selectable markers include those which confer resistance to drugs, such as G418, hygromycin, and methotrexate. Cells stably transfected with the introduced nucleic acid can be identified by drug selection (e.g., cells that have incorporated the selectable marker gene will survive, while other cells die).

A host cell of the invention, such as a prokaryotic or eukaryotic host cell in culture, can be used to produce a polypeptide of the invention. Accordingly, the invention further provides methods for producing a polypeptide of the invention using host cells of the invention. In one embodiment, the method comprises culturing the host cell of invention (into which a recombinant expression vector encoding a polypeptide of the invention has been introduced) in a suitable medium, so that the polypeptide is produced by the cell. In another embodiment, the method further comprises isolating the polypeptide from the culture medium or the host cell.

V. Transgenics

Host cells of the invention can also be used to produce non-human transgenic animals. For example, in one embodiment, a host cell of the invention is a fertilized oocyte or an embryonic stem cell into which a nucleic acid encoding a polypeptide of the invention has been introduced. Such host cells can then be used to generate a non-human transgenic animal into the genome of which an exogenous sequence encoding a polypeptide of the invention has been introduced. These host cells can, alternatively, be used to generate a homologous recombinant animal in which an endogenous nucleic acid encoding a polypeptide of the invention is altered. Such animals are useful for studying the function, the activity, or both, of the polypeptide and are also useful for identifying and evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal. The transgene directs expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell (e.g., an embryonic cell) of the animal prior to development of the animal.

A transgenic animal of the invention can be created by introducing a nucleic acid encoding a polypeptide of the invention (or a homologue thereof) into the male pronucleus of a fertilized oocyte (e.g., by microinjection, retroviral infection, and development of the oocyte in a pseudopregnant female foster animal). Intronic sequences and polyadenylation signals can be included in the transgene in order to increase the efficiency of expression of the transgene. One or more tissue-specific regulatory sequences can be operably linked with the transgene to direct expression of the polypeptide of the invention to particular cells. Methods for generating transgenic animals by embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome, expression of mRNA encoding the transgene in tissues or cells of the animals, or both. A transgenic founder animal can be used to breed additional animals which harbor the transgene. Moreover, transgenic animals harboring the transgene can be bred with other transgenic animals harboring the same or other transgenes.

To generate a homologous recombinant animal, a vector is prepared which contains a nucleic acid of the invention (i.e., encoding at least a portion of MLip-1). A deletion, addition, or substitution can be introduced into the nucleic acid to alter expression of the nucleic acid or a property (e.g., tissue level or activity) of the encoded polypeptide. For example, the vector can be designed such that, upon homologous recombination, the endogenous nucleic acid is functionally disrupted (i.e., no longer encodes a functional protein). Such vectors are colloquially referred to as "knock-out" vectors, and animals generated using such vectors are designated "knock-out" animals. Alternatively, the vector can be designed such that, upon homologous recombination, the endogenous gene is mutated or otherwise altered but still encodes functional protein (e.g., the upstream regulatory region can be altered to affect expression of the endogenous protein). In the homologous recombination vector, the altered portion of the gene is flanked at its 5' and 3' ends by additional nucleic acid of the gene to permit homologous recombination to occur between the exogenous gene carried by the vector and an endogenous nucleic acid (e.g. an endogenous gene) in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). Selected cells are injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can be implanted into a suitable pseudopregnant female foster animal, and the resulting embryo can be carried to term by the foster animal. Progeny harboring the homologously recombined DNA in their germ cells can be used to breed animals in which all cells of the animal contain the homologously recombined DNA (i.e., by germline transmission of the transgene). Methods for constructing homologous recombination vectors and homologous recombinant animals are described further in Bradley (1991) *Current Opinion in Bio/Technology* 2:823–829 and in PCT publications WO 90/11354, WO 91/01140, WO 92/0968, and WO 93/04169.

In another embodiment, transgenic non-human animals are generated in which the transgene comprises a system for regulating expression of the transgene. An example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombination system is the FLP recombinase system of Saccharomyces cerevisiae (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided by constructing "double" transgenic animals, e.g., by mating two transgenic animals, one containing a transgene encoding a selected protein and the other containing a transgene encoding a recombinase.

Clones of non-human transgenic animals described herein can be produced, for example, according to the methods described in Wilmut et al. (1997) *Nature* 385:810–813 and PCT Publication numbers WO 97/07668 and WO 97/07669.

VI. Pharmaceutical Compositions

The nucleic acids, polypeptides, antibodies, vectors, and host cells (also referred to herein as "active agents") of the invention can be incorporated into pharmaceutical compositions suitable for administration to a patient. Such compositions typically comprise the agent and a pharmaceutically acceptable carrier. As used herein the language "pharmaceutically acceptable carrier" is intended to include any and all solvents, dispersion media, coatings, antibacterial and anti-fungal agents, isotonic and absorption delaying agents, and the like, that are compatible with pharmaceutical administration. The use of such media and agents for pharmaceutically active substances is well known in the art. Except insofar as any conventional media or agent is incompatible with an active agent of the invention, use thereof in the pharmaceutical compositions of the invention is contemplated. Supplementary active compounds can also be incorporated into the compositions.

The invention includes methods for preparing pharmaceutical compositions for modulating expression, activity, or level of activity (e.g., in a tissue or body fluid) of a polypeptide or nucleic acid of the invention. Such methods comprise formulating a pharmaceutically acceptable carrier with an agent which modulates expression, activity, or activity level of a polypeptide or nucleic acid of the invention. Such compositions can further include additional active agents. Thus, the invention further includes methods for preparing a pharmaceutical composition by formulating a pharmaceutically acceptable carrier with an agent that modulates expression or activity of a polypeptide or nucleic acid of the invention and one or more additional active compounds.

The agent which modulates expression, activity, or activity level can, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents, protein or polypeptide agents, antibody substances, and other active agents of the invention depends upon a number of factors within the ken of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject weight or sample weight (e.g., about 1 nanogram per kilogram to about 500 milligrams per kilogram, about 100 micrograms per kilogram to about 5 milligrams per kilogram, or about 1 microgram per kilogram to about 50 micrograms per kilogram).

Exemplary doses of a protein or polypeptide include gram, milligram, or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). For antibodies, the preferred dosage is about 0.1 milligrams per kilogram to 100 milligrams per kilogram of body weight (generally about 10 milligrams per kilogram to 20 milligrams per kilogram). If the antibody is to act in the brain, a dosage of about 50 milligrams per kilogram to 100 milligrams per kilogram is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. (1997, *J. Acquired Immune Deficiency Syndromes and Human Retrovirology* 14:193).

It is furthermore understood that appropriate doses of one of these agents depend upon the potency of the agent with respect to the expression or activity to be modulated. Such appropriate doses can be determined using the assays described herein. When one or more of these agents is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation or ingestion), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates; and agents for adjustment of tonicity such as sodium chloride or dextrose. pH can be adjusted using acids or bases, such as hydrochloric acid or sodium hydroxide. The parenteral preparation can be enclosed in ampules, disposable syringes, or multiple dose vials made of glass or plastic.

Pharmaceutical compositions suitable for injectable use include sterile aqueous solutions (i.e., where the agent is water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), and phosphate buffered saline (PBS). In each instance, the composition should be sterile and should be fluid to the extent that easy syringability exists. It should also be stable under the conditions of manufacture and storage and preferably includes a preservative to prevent contamination by microorganisms such as bacteria and fungi. The carrier can be a solvent or dispersion medium containing, for example, water, ethanol, a polyol (e.g., glycerol, propylene glycol, liquid polyethylene glycol, or the like), and suitable mixtures thereof. The proper fluidity can be maintained, for example, by the use of a coating such as lecithin, by the maintenance of the required particle size in the case of dispersion and by the use of surfactants. Growth or survival of microorganisms can be prevented by including one or more anti-bacterial and antifungal agents (e.g., parabens, chlorobutanol, phenol, ascorbic acid, thimerosal, or the like) in the composition. Prolonged absorption of the injectable compositions can, be achieved by including in the composition an agent which delays absorption, such as aluminum monostearate or gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating other ingredients such as one or more of those enumerated above. In the case of sterile powders for preparation of sterile injectable solutions, preferred methods of preparation include vacuum drying and freeze-drying. Each of these methods yields a powder comprising the active ingredient and any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared in a fluid carrier for use, for example, as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose; a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of a dispersed powder or an aerosol spray from a pressurized container or dispenser which contains a suitable propellant, e.g., a gas such as carbon dioxide, or a nebulizer.

Systemic administration can also be achieved using transmucosal or transdermal delivery methods. For transmucosal or transdermal administration, penetrants appropriate to the barrier to be permeated are used in the formulation. Such penetrants are generally known in the art and include, for example, detergents, bile salts, and fusidic acid derivatives. Transmucosal administration can be accomplished using nasal sprays, swabs, suppositories, or other intranasal dosage forms or applicators. For transdermal administration, the active compounds can be formulated as ointments, salves, gels, creams, wound dressings, patches, or the like.

The compounds can also be prepared in the form of suppositories (e.g., using conventional suppository bases such as cocoa butter and other glycerides) or retention enemas for rectal delivery.

In one embodiment, the active compounds are prepared using carriers that protect the compound against rapid elimination from the body, such as a controlled release formulation. Exemplary controlled release formulations include implants and microencapsulated delivery systems. Biodegradable, biocompatible polymers can be used in such implants and systems, including, for example, ethylene vinyl acetate, polyanhydrides, polyglycolic acid, collagen, polyorthoesters, and polylactic acid. Methods for preparation of such formulations are known in the art. The materials can also be obtained from commercial entities such as Alza Corporation and Nova Pharmaceuticals, Inc. Liposomal suspensions (including liposomes having monoclonal antibodies incorporated therein or at the liposomal surface) can be used as pharmaceutically acceptable carriers in the pharmaceutical compositions of the invention. These can be prepared according to methods known to those skilled in the art, for example, as described in U.S. Pat. No. 4,522,811.

Oral or parenteral compositions in dosage unit form are preferred for ease of administration and uniformity of dosage. "Dosage unit form," as used herein, refers to physically discrete units suitable for administration as complete, individual dosages for the subject to be treated. Each unit contains a pre-selected quantity of active agent of the invention in association with a suitable pharmaceutically acceptable carrier, wherein the quantity is calculated to produce a desired therapeutic effect. The quantity of the active agent and the form of the dosage unit are dictated by and directly dependent on the unique characteristics of the active agent, the particular therapeutic effect to be achieved, and the limitations inherent in the art of compounding such an active agent for the treatment of individuals.

Nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is embedded. Alternatively, where the complete gene delivery vector can be produced intact from recombinant cells (e.g., as with retroviral vectors) the pharmaceutical preparation can include one or more cells which produce the gene delivery system.

The pharmaceutical compositions can be included in a container, pack, or dispenser together with instructions for administration.

VII. Uses and Methods of the Invention

Nucleic acids, polypeptides, small molecules, and antibodies described herein can be used in one or more of the following methods: a) screening assays; b) detection assays (e.g., chromosomal mapping, tissue typing, and forensic biology assays); c) predictive medicine (e.g., diagnostic assays, prognostic assays, monitoring of clinical trials, and pharmacogenomic applications); and d) methods of treatment (e.g., therapeutic and prophylactic methods). For example, polypeptides of the invention can to used for all of the purposes identified herein in portions of the disclosure relating to individual types of protein of the invention (e.g., MLip-1 proteins and derivatives, fragments, and variants thereof; i.e., "MLip-1-related polypeptides"). Isolated nucleic acids of the invention and nucleic acids encoding MLip-1-related polypeptides can be used to express polypeptides (e.g., using a recombinant expression vector in a host cell for gene therapy applications), to detect mRNA (e.g., in a biological sample) or a genetic lesion, and to modulate the level of activity of a polypeptide of the invention in a cell or tissue. In addition, the polypeptides of the invention can be used to screen drugs or compounds which modulate activity or expression of MLip-1 and to treat disorders characterized by insufficient or excessive production of MLip-1 or production of a form of MLip-1 which has decreased or aberrant activity compared to the wild type protein.

This invention includes novel pharmacological agents identified by the above-described screening assays and uses of such agents for treatments as described herein.

A. Screening Assays

The invention provides a method (also referred to herein as a "screening assay") for identifying modulators, i.e., candidate or test compounds or agents (e.g., peptides, peptidomimetics, antibody substances, small molecules, or other drugs) which bind with MLip-1 or another polypeptide of the invention, or have a stimulatory or inhibitory effect on, for example, expression or activity of MLip-1 or another polypeptide of the invention.

In one embodiment, the invention provides assays for screening candidate or test compounds which bind with or modulate activity of MLip-1 protein or a biologically active portion thereof. The test compounds of the present invention can be obtained using any of numerous approaches known in combinatorial library methods known in the art. Known types of combinatorial libraries include: biological libraries; spatially addressable parallel solid phase or solution phase libraries; synthetic library methods requiring deconvolution; the "one-bead one-compound" library method; and synthetic library methods using affinity chromatography selection. The biological library approach is generally limited to peptide libraries, while the other four approaches are applicable to peptide, non-peptide oligomer, or small molecule libraries of compounds (Lam (1997) *Anticancer Drug Des.* 12:145).

Examples of methods for making molecular libraries are found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In one embodiment, the invention includes a cell-based assay involving a cell which expresses a membrane-bound form of a polypeptide of the invention, or a biologically active portion thereof, on the cell surface. The cell is contacted with a test compound, and the ability of the test compound to bind with the polypeptide is determined. The cell, for example, can be a yeast cell or a cell of mammalian origin. Determining the ability of the test compound to bind with the polypeptide can be accomplished, for example, by coupling the test compound with a radioisotope or enzymatic label such that binding of the test compound with the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred screening method, a cell which expresses a cell-bound form of a polypeptide of the invention (e.g., MLip-1 protein lacking a signal sequence cleavage site), or a biologically active portion thereof, on its surface is contacted with a compound which is known to bind with or-known to be a substrate for the polypeptide in an assay mixture. The assay mixture is contacted with a test compound, and the ability of the test compound to interact with the polypeptide is determined. Ability of the test compound to interact with the polypeptide can be assessed by determining the ability of the test compound to preferentially bind with the polypeptide relative to the known compound or by determining the ability of the test compound to catalyze conversion of the known compound to a different compound.

In another embodiment, the assay involves assessment of an activity characteristic of a polypeptide of the invention, wherein binding of the test compound with the polypeptide or biologically active portion thereof alters (i.e., increases or decreases) the activity of the polypeptide. For example, the method described in Giller et al. (1992, J. Biol. Chem. 267:16509–16516) or any other known method for evaluating lipase activity (e.g., the LIPASE-PST™ kit, Sigma Chemical Co., St. Louis, Mo.) may be used to assess lipase activity in a cell expressing a nucleic acid encoding a nucleic acid of the invention or in a medium in which the cell is grown. In this assay, a test cell which expresses a nucleic acid encoding a polypeptide of the invention (i.e., in either a membrane-bound or a secreted form) is contacted with a fluid containing a labeled lipase substrate (e.g., a tritiated triglyceride or the Sigma Lipase-PS™ substrate reagent), and release of the label from the substrate is assessed. For example, cultured HeLa cells can be transfected with a recombinant Vaccinia virus vector comprising a nucleic acid encoding a polypeptide of the invention. A tritiated triglyceride is added to the medium, and the medium containing the labeled compound is rinsed from the cells after a selected amount of time. The tritium content of the cells (i.e., corresponding to uptake by the cell of a tritiated fatty acid) or the tritiated fatty acid (or glycerol compound, depending on the site of tritiation) is assessed using, for example, a liquid chromatography device coupled with a scintillation counter. The skilled artisan will understand how this assay can be modified to accommodate particular test cells, nucleic acid vectors, and particular mono-, di-, and tri-glycerides, as well as lipids derived from various glycerol compounds (e.g., glycerol, glycerol phosphates, alkyl glyceryl ethers, glycerol phosphoryl-choline, glycerol phosphoryl-serine, glycerol phosphoryl-ethanolamine, and the like).

In another embodiment, an assay is a cell-based assay comprising contacting a cell expressing a cell membrane-bound form of a polypeptide of the invention (e.g. MLip-1 protein lacking a signal sequence cleavage site), with a test compound and determining the ability of the test compound to modulate (e.g., stimulate or inhibit) the activity of the polypeptide or biologically active portion thereof. Determining the ability of the test compound to modulate the activity of the polypeptide or biologically active portion thereof can be accomplished, for example, by determining the ability of the polypeptide to bind with or interact with a target molecule or to transport lipids or fatty acyl moieties across the cytoplasmic membrane or to incorporate them into the membrane. An analogous cell-free assay may be performed using a mature MLip-1 protein or another non-cell-bound form of a polypeptide of the invention, wherein the ability of the polypeptide to catalyze formation or hydrolysis of ester bonds between a glycerol moiety and a fatty acyl moiety is assessed.

Determining the ability of a polypeptide of the invention to bind with or interact with a target molecule can be accomplished by one of the methods described above for determining direct binding. As used herein, a "target molecule" is a molecule with which a selected polypeptide (e.g., mature MLip-1 protein) binds or interacts with in nature, for example, a molecule on the surface of a cell which expresses the selected protein, a molecule on the surface of a second cell, a molecule in the extracellular milieu, or a molecule associated with a plasma lipoprotein particle In yet another embodiment, a screening assay of the present invention is a cell-free assay comprising contacting a polypeptide of the invention (e.g., MLip-1 protein or a biologically active portion thereof) with a test compound and determining the ability of the test compound to bind with the polypeptide. Binding of the test compound with the polypeptide can be determined either directly or indirectly, as described above. In one embodiment, the assay includes contacting the polypeptide with a known compound which binds the polypeptide to form an assay mixture, contacting the assay mixture with a test compound, and determining the ability of the test compound to interact with the polypeptide. Ability of the test compound to interact with the polypeptide comprises determining the ability of the test compound to preferentially bind with the polypeptide, relative to the ability of the known compound to bind therewith.

In one or more embodiments of the above assay methods of the present invention, it can be desirable to immobilize either a polypeptide of the invention or a target molecule thereof in order to facilitate separation of complexed from non-complexed forms of either the polypeptide or the target molecule. Immobilization of assay components also facilitates automation of the assay. Binding of a test compound with the polypeptide, or interaction of the polypeptide with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided which has a domain that facilitates binding of the protein with a matrix. For example, glutathione-S-transferase fusion proteins can be adsorbed onto glutathione Sepharose™ beads (Sigma Chemical; St. Louis, Mo.) or glutathione-derivatized microtiter plates. Such fusion proteins can be combined with the test compound, and the mixture is incubated under conditions conducive to protein-ligand complex formation or protein activity (e.g., at physiological conditions for salt and pH). Following incubation, the beads or microtiter plate wells are washed to remove any non-bound components and one or both of complex formation and lipase activity is measured either directly or indirectly, for example, as described above. Alternatively, the complexes can be dissociated from the matrix, and the level of binding or activity of the polypeptide of the invention can be determined using standard techniques.

Other techniques for immobilizing a protein on a matrix can be used in the screening assays of the invention. For example, a polypeptide of the invention can be immobilized utilizing conjugation of biotin and streptavidin. Biotinylated polypeptides can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with polypeptides but which do not interfere with binding of the polypeptides to a target molecule (e.g., an enzymatic substrate such as a triacylglyceride) can be derivatized to the wells of the plate, and non-bound polypeptide of the invention can be trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention (e.g., hydrolysis of a labeled triacylglyceride).

In another embodiment, modulators of expression of a polypeptide of the invention are identified in a method in which a cell is contacted with a test compound and expression of mRNA or encoding MLip-1 or MLip-1 protein in the cell is determined. The level of expression of MLip-1 mRNA or protein in the presence of the test compound is compared with the level of expression of the mRNA or protein in the absence of the test compound. The test compound can then be identified as a modulator of expression of MLip-1 based on this comparison. For example, when expression of MLip-1 mRNA or protein is greater (i.e., statistically significantly greater) in the presence of the test compound than in its absence, the test compound is identified as a stimulator of MLip-1 mRNA or protein expression. Alternatively, when expression of MLip-1 mRNA or protein is less (i.e., statistically significantly less) in the presence of the test compound than in its absence, the test compound is identified as an inhibitor of MLip-1 mRNA or protein expression. The level of MLip-1 mRNA or protein expression in the cells can be determined by methods described herein.

In yet another aspect of the invention, a polypeptide of the invention can be used as a "bait protein" in a two-hybrid assay or three hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication number WO 94/10300), to identify other proteins, which bind with or interact with the polypeptide of the invention and modulate activity of the polypeptide. Such binding proteins are also likely to be involved in the propagation of signals by the polypeptide as, for example, upstream or downstream elements of a signaling pathway involving the polypeptide.

This invention further pertains to novel agents identified by the above-described screening assays and uses thereof for treatments as described herein.

B. Detection Assays

Portions or fragments of the nucleic acids identified herein (including entire nucleic acids, i.e. wherein the portion is the entirety of a nucleic acid) can be used in numerous ways as polynucleotide reagents. For example, such nucleic acids can be used to: (i) map the MLip-1 gene on a chromosome and, thus, locate MLip-1 gene regions associated with genetic disease; (ii) identify an individual from a minute biological sample (tissue typing); and (iii) aid in forensic identification of a biological sample. These applications are described in the subsections below.

1. Chromosome Mapping

All or a portion of a nucleic acid encoding MLip-1 (e.g. a nucleic acid having a nucleotide sequence consisting of all or a portion of SEQ ID NO: 1 or 2) can be used to map the location of the gene on a chromosome. Mapping of the sequence to a chromosome can be used to associate MLip-1 with one or more diseases.

Briefly, the MLip-1 gene can be mapped to a chromosome by preparing PCR primers (preferably 15 to 25 nucleotide residues in length) from the sequence of a nucleic acid of the invention. Computer analysis of the sequence of a nucleic acid of the invention can be used to rapidly select primers that do not span more than one exon in the genomic DNA, as these could complicate the amplification process. The primers can then be used for PCR screening of somatic cell hybrids containing individual human chromosomes. Only hybrids containing the human gene corresponding to the gene sequences will yield an amplified fragment. For a review of this technique, see D'Eustachio et al. (1983, *Science* 220:919–924).

PCR mapping of somatic cell hybrids is a rapid procedure for assigning a particular sequence to a particular chromosome. Three or more sequences can be assigned per day using a single thermal cycler. Using the nucleotide sequences of one or more of the nucleic acids of the invention to design oligonucleotide primers, sub-localization can be achieved using panels of fragments obtained from specific chromosomes. Other mapping strategies which can be used to map a gene to its chromosome include in situ hybridization (described in Fan et al. (1990) *Proc. Natl. Acad. Sci. USA* 87:6223–27), pre-screening using labeled flow-sorted chromosomes, and pre-selection by hybridization to chromosome specific cDNA libraries. Fluorescence in situ hybridization (FISH) of a DNA sequence with a metaphase chromosomal spread can be used to provide a precise chromosomal location in one step. For a review of this technique, see Verma et al. ("Human Chromosomes: A Manual of Basic Techniques", Pergamon Press, New York, 1988).

Reagents for chromosome mapping can be used individually to mark a single chromosome or a single site on a chromosome. Alternatively, panels of reagents can be used for marking multiple sites or multiple chromosomes. Reagents corresponding to non-coding regions of the genes are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified using linkage analysis (i.e., analysis of co-inheritance of physically adjacent genes), described in, e.g., Egeland et al. (1987) *Nature* 325:783–787.

Moreover, differences in genomic nucleotide sequences between individuals afflicted and not afflicted with a disease associated with the MLip-1 gene can be determined. If a mutation is observed in some or all of the afflicted individuals but not in any non-afflicted individuals, then the mutation is likely to be a causative agent of the disease, or at least strongly associated with occurrence of the disease. Comparison of afflicted and non-afflicted individuals generally involves first looking for structural alterations in chromosomes obtained from patients of the two groups. Exemplary structural alterations include deletions and translocations that are visible from chromosome spreads or detectable using PCR amplification of all or part of the MLip-1 gene. Ultimately, complete sequencing of genes from several individuals can be performed to confirm the presence of a mutation and to distinguish mutations from polymorphisms.

2. Tissue Typing

Nucleotide sequences of the nucleic acids of the invention can be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed by Southern blotting to yield individually unique bands which can be used for identification. This method does not exhibit the current limitations of the "dog tags" identification system, in which identification devices can be lost, switched, or stolen, making positive identification difficult. The sequences of the nucleic acids of the invention are useful as additional DNA markers for RFLP (described in U.S. Pat. No. 5,272,057).

Furthermore, the sequences of the nucleic acids of the invention can be used to provide an alternative technique which determines the DNA sequence of selected portions of an individual's genome. Thus, the nucleic acid sequences described herein can be used to prepare pairs of PCR primers for amplification of at least a portion of a human genome. These primer pairs can be used to amplify an individual's DNA and subsequently sequence it.

Panels of corresponding DNA sequences obtained from individuals, prepared in this manner, can provide unique individual identifications, as each individual will have a unique set of such DNA sequences, owing in part to allelic differences. The sequences of the nucleic acids of the invention can be used to obtain such identification sequences from individuals and from tissue. The nucleotide sequences of the invention uniquely represent portions of the human genome. Allelic variation occurs to some degree in the coding regions of these sequences, and to a greater degree in the non-coding regions. It is estimated that allelic variation between individual humans occurs with a frequency of about once every 500 base pairs. Each of the sequences described herein can be used as a standard against which DNA obtained from an individual can be compared for identification purposes. Because greater numbers of polymorphisms occur in the non-coding regions, fewer sequences are necessary to differentiate individuals. Non-coding portions of SEQ ID NO: 1 can provide positive individual identification with a panel of about 10 to 1,000 primers each of which yields a non-coding amplified sequence of 100 bases. If a predicted coding sequence, such as one in SEQ ID NO: 2 is used, a more appropriate number of primers for positive individual identification would be about 500–2,000.

If a panel of nucleic acid reagents having the nucleotide sequences described herein is used to generate a unique identification database for an individual, then the same reagents can be used later to identify tissue from that individual. Using the unique identification database, positive identification of the individual, living or dead, can be made using extremely small tissue samples.

3. Use of Partial Gene Sequences in Forensic Biology

DNA-based identification techniques can be used in forensic biology. Forensic biology is a scientific field employing genetic typing of biological evidence recovered at a crime scene as a means for positively identifying, for example, a perpetrator of a crime. To make such an identification, PCR technology can be used to amplify nucleic acid obtained from very small biological samples such as tissues (e.g., hair or skin) or body fluids (e.g., blood, saliva, or semen) recovered at a crime scene. The amplified sequence can be compared with a standard, allowing identification of the origin of the biological sample.

The nucleotide sequences of the present invention can be used to generate polynucleotide reagents (e.g., PCR primers) targeted to specific loci (e.g., the MLip-1 gene) in the human genome, which can enhance the reliability of DNA-based forensic identifications by, for example, providing another "identification marker" (i.e., another DNA sequence that is unique to a particular individual). As mentioned above, nucleotide sequence information can be used for identification as an accurate alternative to patterns formed by restriction enzyme generated fragments. Sequences corresponding to non-coding regions are particularly appropriate for this use, because greater numbers of polymorphisms and mutations occur in non-coding regions than in coding regions, making it easier to differentiate individuals using this technique. Examples of polynucleotide reagents include nucleic acids of the invention such as MLip-1 gene fragments derived from non-coding regions of the gene and having a length of at least 20 or 30 bases.

Nucleotide sequences described herein can further be used to generate polynucleotide reagents, e.g., labeled or label-able probes which can be used in, for example, in situ hybridization techniques, to identify a specific tissue, e.g., pancreas tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine, in which diagnostic assays, prognostic assays, pharmacogenomics, and monitoring clinical trails are used for prognostic (predictive) purposes to treat an individual prophylactically. Accordingly, one aspect of the present invention relates to diagnostic assays for assessing expression of a polypeptide or nucleic acid of the invention. Such assays can also be used to assess activity of a polypeptide of the invention in the context of a biological sample (e.g., blood, serum, cells, tissue). Each of these diagnostic assays is useful for determining whether an individual is afflicted with a disease or disorder associated with aberrant expression or activity of MLip-1 protein, or is at risk of developing such a disorder. By way of example, mutations in a gene corresponding to a nucleic acid of the invention can be assayed in a biological sample. Such assays can be used for prognostic or predictive purpose to treat an individual prior to onset of a disorder characterized by or associated with aberrant expression or activity of MLip-1 protein.

Another aspect of the invention provides methods for assessing expression of a nucleic acid or polypeptide of the invention and methods for assessing activity of a polypeptide of the invention in an individual. These assays can be used to select appropriate therapeutic or prophylactic agents for that individual. A selection process of this sort is referred to herein and in the art as "pharmacogenomics." Pharmacogenomics enables selection of agents (e.g., drugs) for therapeutic or prophylactic treatment of an individual based on the genotype of the individual. In these methods, the genotype of the individual is examined to determine the ability of the individual to respond favorably to administration of a particular agent.

Yet another aspect of the invention pertains to monitoring the influence of one or more agents (e.g., drugs or other compounds) on expression or activity of a polypeptide of the invention in clinical trials. These and other methods are described in further detail in the following sections.

1. Diagnostic Assays

An exemplary method for detecting the presence or absence of a polypeptide or nucleic acid of the invention in a biological sample involves obtaining a biological sample from a subject and contacting the biological sample with a compound or an agent capable of detecting the polypeptide or nucleic acid (e.g., mRNA, genomic DNA) such that the presence of the polypeptide or nucleic acid is detected in the biological sample. A preferred agent for detecting mRNA or genomic DNA encoding MLip-1 protein is a labeled polynucleotide probe capable of hybridizing with mRNA or genomic DNA encoding the polypeptide. The nucleic acid probe can be, for example, a full-length cDNA, such as the nucleic acid of SEQ ID NO: 1 or a portion thereof, such as an oligonucleotide of at least 15, 30, 50, 56, 100, 250 or 500 nucleotides in length which specifically hybridizes under stringent conditions with an mRNA or genomic DNA encoding MLip-1 protein. Other suitable probes for use in the diagnostic assays of the invention are described herein.

A preferred agent for detecting a polypeptide of the invention is an antibody capable of binding specifically with the polypeptide, such as an antibody substance comprising a detectable label. Antibodies can be polyclonal, or more preferably, monoclonal. An intact antibody, a fragment of an antibody (e.g., a Fab or F(ab')$_2$ fragment), a T cell receptor or fragment thereof, or another immunoglobulin which binds specifically with an epitope of MLip-1 can be used. The term "labeled", with regard to the antibody substance, encompasses direct labeling of the antibody substance by coupling (i.e., physically linking) a detectable substance with the antibody substance, as well as indirect labeling of the antibody substance. Examples of indirect labeling include detection of a primary antibody using a fluorescently labeled secondary antibody (i.e., one which binds specifically with the first antibody or with antibodies of the same type). The term "biological sample" is intended to include tissues, cells, and biological fluids isolated from a subject, as well as tissues, cells, and fluids present within a subject. That is, the detection method of the invention can be used to detect mRNA, protein, or genomic DNA in a biological sample in vitro as well as in vivo. For example, in vitro techniques for detection of mRNA include Northern hybridization and in situ hybridizations. In vitro techniques for detection of a polypeptide of the invention include enzyme linked immunosorbent assay (ELISA), Western blotting, immunoprecipitation, and immunofluorescence detection. In vitro techniques for detection of genomic DNA include, for example, Southern hybridization. Furthermore, in vivo techniques for detection of a polypeptide of the invention include introducing into a subject a labeled antibody directed against the polypeptide. For example, the antibody can be labeled with a radioactive marker, the presence and location of which can be detected in a subject by standard imaging techniques involving, for example, imaging using a 'gamma camera' detector of gamma radiation.

In one embodiment, the biological sample contains protein molecules obtained from a subject. Alternatively, the biological sample can contain mRNA molecules obtained from a subject or genomic DNA molecules obtained from the subject. A preferred biological sample is a tissue (e.g., a pancreatic tissue) sample or a body fluid sample (e.g. gastric juice) isolated by conventional means' from a subject.

In another embodiment, the methods of the invention involve obtaining a control biological sample from a control subject, contacting the control sample with a compound or agent capable of detecting a polypeptide of the invention, or an mRNA or genomic DNA encoding a polypeptide of the invention, such that the presence of the polypeptide or an mRNA or genomic DNA encoding such a polypeptide is detected in the biological sample. The presence of the polypeptide, mRNA, or genomic DNA encoding the polypeptide in the control sample can be compared with the presence of the polypeptide or mRNA or genomic DNA encoding the polypeptide in the test sample. This method is useful, for example, for comparing levels of protein and RNA in a sample obtained from a patient who is suspected of being afflicted with an MLip-1 associated disorder with the corresponding levels in a normal (i.e., non-afflicted) patient. This method is also useful for detecting the presence of a normal or mutant allele of the MLip-1 gene in a patient.

The invention also encompasses kits for detecting the presence of a polypeptide or nucleic acid of the invention in a biological sample. Such kits can be used to determine if a subject is afflicted with or is at increased risk of developing a disorder associated with aberrant expression of MLip-1 protein. For example, the kit can comprise a labeled compound or agent capable of detecting a polypeptide or nucleic acid of the invention in a biological sample and means for determining the amount of the labeled compound that interacts with the polypeptide or nucleic acid in the sample (e.g., an antibody which binds the polypeptide or an oligonucleotide probe which binds with DNA or mRNA encoding the polypeptide). Kits can include instructions for assessing whether a subject is suffering from or is at risk of developing a disorder associated with aberrant expression of MLip-1 protein if the amount of the polypeptide or mRNA encoding the polypeptide is above or below a normal level.

For antibody-based kits, the kit can comprise, for example: (1) a first antibody (e.g., attached to a solid support) which binds with a polypeptide of the invention; and (2) a second, different antibody which binds with either the polypeptide or the first antibody and is conjugated with a detectable agent.

For oligonucleotide-based kits, the kit can comprise, for example: (1) an oligonucleotide (e.g., a detectably labeled oligonucleotide) which hybridizes with a nucleic acid of the invention or (2) a pair of primers useful for amplifying a nucleic acid of the invention. The kit can also comprise, e.g., a buffering agent, a preservative, or a protein stabilizing agent. The kit can also comprise components, necessary for detecting the detectable agent (e.g., an enzyme, a substrate, a scintillation cocktail, etc.). The kit can also contain one or more control samples which can be assayed and compared with results obtained using the test sample. Each component of the kit can be enclosed within an individual container and all of the various containers can be within a single package, optionally together with instructions for assessing whether the subject is suffering from or is at risk of developing a disorder associated with aberrant expression or activity of MLip-1 protein.

2. Prognostic Assays

The methods described herein can be used as diagnostic or prognostic assays to identify subjects at risk of developing a disease or disorder associated with aberrant expression or activity of MLip-1 protein. Thus, the present invention provides a method in which a biological sample is obtained from a subject and a polypeptide or nucleic acid (e.g., mRNA or genomic DNA) of the invention is detected in the sample. The presence of an aberrant MLip-1 polypeptide or nucleic acid or detection of an aberrant level of MLip-1 expression or activity is an indication that the subject is predisposed to become afflicted with (i.e., is at an increased risk of developing) an MLip-1-associated disorder Furthermore, the prognostic assays described herein can be used to determine whether a subject can be administered an agent (e.g., an agonist, antagonist, peptidomimetic, protein, peptide, antibody substance, nucleic acid, small molecule, or other drug candidate) to treat an MLip-1-associated disease or disorder prior to onset or worsening of the disease or disorder or a symptom thereof. For example, such methods can be used to determine whether a subject can be effectively treated using a specific agent or class of agents (e.g., agents of a type which decrease MLip-1 activity).

The methods of the invention can be used to detect genetic lesions or mutations in an MLip-1 gene, thereby determining if a subject having the lesioned gene is at risk for developing a disorder characterized by aberrant expression or activity of MLip-1 protein. In preferred embodiments, the methods include detecting, in a sample of cells obtained from the subject, the presence or absence of a genetic lesion or mutation characterized by at least one of an alteration affecting the integrity of a gene encoding the polypeptide of the invention and mis-expression of a gene encoding a polypeptide of the invention. For example, such genetic lesions or mutations can be detected by assessing the existence of one or more of: 1) a deletion of one or more nucleotide residues from the MLip-1 gene; 2) an addition of one or more nucleotide residues to the MLip-1 gene; 3) a substitution of one or more nucleotide residues of the MLip-1 gene; 4) a chromosomal rearrangement of the MLip-1 gene; 5) an alteration in the level of a messenger RNA transcript of the MLip-1 gene; 6) an aberrant modification of the MLip-1 gene, such as a modification of the methylation pattern of the gene; 7) the presence of a non-wild type splicing pattern of a messenger RNA transcript of the MLip-1 gene; 8) the presence of a non-wild type level of MLip-1 protein; 9) an allelic loss of the MLip-1 gene; and 10) an inappropriate post-translational modification of the protein encoded by the MLip-1 gene. As described herein, for example, there are a large number of assay techniques known in the art which can be used for detecting lesions in a gene.

In certain embodiments, detection of the lesion involves the use of a probe/primer in a polymerase chain reaction (see, e.g., U.S. Pat. Nos. 4,683,195 and 4,683,202). Exemplary methods of this type include anchor PCR, RACE PCR, or, alternatively, a ligation chain reaction (LCR; see, e.g., Landegran et al. (1988) *Science* 241:1077–1080; and Nakazawa et al. (1994) *Proc. Natl. Acad. Sci. USA* 91:360–364). LCR can be particularly useful for detecting point mutations in a gene (see, e.g., Abravaya et al. (1995) *Nucleic Acids Res.* 23:675–682). Detection of an MLip-1 gene lesion can involve collecting a sample of cells from a patient, isolating a nucleic acid (e.g., genomic, mRNA, or both) from cells of the sample, contacting the nucleic acid with one or more primers which specifically hybridize with the MLip-1 gene under conditions such that hybridization and amplification of the gene (if it is present) occurs, and detecting the presence or absence of an amplification product. Alternatively, the size of the amplification product can be assessed and compared with: the length of the corresponding amplification product in a control sample. PCR, LCR, or both, can be desirable to use as a preliminary amplification step in conjunction with any of the other techniques used for detecting mutations described herein.

Alternative amplification methods include: self-sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, which can be followed by detection of the amplified portion using techniques known in the art. Detection methods are preferably able to detect nucleic acid molecules present in very low numbers.

In an alternative embodiment, mutations in the MLip-1 gene of a cell are identified by one or more alterations in restriction enzyme cleavage patterns of a nucleic acid obtained from the cell. For example, sample and control DNA is isolated, (optionally) amplified, digested with one or more restriction endonucleases, and fragment length sizes are determined by gel electrophoresis and compared. Differences in fragment length sizes between sample and control DNA digestion mixtures indicates that one or more mutations have occurred in the sample DNA. Use of sequence specific ribozymes (see, e.g., U.S. Pat. No. 5,498,531) can be used to score nucleic acids for the presence of specific mutations by assessing the presence or absence of a ribozyme cleavage site in a sample nucleic acid.

In other embodiments, genetic mutations are identified by hybridizing sample and control nucleic acids, e.g., DNA or RNA, with high density arrays containing hundreds or thousands of oligonucleotides probes (Cronin et al. (1996) *Human Mutation* 7:244–255; Kozal et al. (1996) *Nature Medicine* 2:753–759). For example, genetic mutations can be identified using two-dimensional arrays of polynucleotides containing light-generated DNA probes as described in Cronin et al., supra. Briefly, a first array of probes comprising sequential overlapping probes differing in frame by a single nucleotide residue can be used to scan long stretches of DNA in a sample. Nucleotide sequence differences between the sample nucleic acid and the sequences of first array probes are detectable as less stringent hybridization between the sample nucleic acid and portions of the array. This step allows the identification of point mutations. This step is followed by hybridization of the sample nucleic acid with a second oligonucleotide array that allows the characterization of specific mutations. These second arrays are smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art is used to directly sequence all or a portion of the MLip-1 gene and detect mutations by comparing the sequence of the sample nucleic acids with the corresponding wild-type (i.e., normal, control) sequence. Examples of sequencing reactions include those based on techniques developed by Maxim and Gilbert (1977, *Proc. Natl. Acad. Sci. USA* 74:560) or Sanger (1977, *Proc. Natl. Acad. Sci. USA* 74:5463). It is also contemplated that any of a variety of automated sequencing procedures can be utilized when performing the diagnostic assays (e.g., (1995) *Bio/Techniques* 19:448), including sequencing by mass spectrometry (see, e.g., PCT Publication number WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the MLip-1 gene include methods in which protection from cleavage agents is used to detect mismatched bases in RNA/RNA or RNA/DNA heteroduplexes (e.g., Myers et al. (1985) *Science* 230:1242). In general, the technique of mismatch cleavage entails generating heteroduplexes formed by hybridizing (preferably labeled) RNA or DNA containing the wild-type sequence with RNA or DNA obtained from a sample such as a patient sample. The resulting double-stranded duplexes are treated with an agent which cleaves single-stranded regions of the duplex. Single stranded regions exist at sites of base pair mismatches between the control and sample strands. For example, RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated (e.g., by size on denaturing polyacrylamide gels), and the fragments are analyzed to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (e.g., DNA mismatch repair enzymes) in defined systems for detecting and mapping point mutations in cDNAs obtained from samples of cells. For example, mutY enzyme of *E. coli* cleaves A residues at G/A mismatches, and thymidine DNA glycosylase from HeLa cells cleaves T residues at G/T mismatches (Hsu et al. (1994) *Carcinogenesis* 15:1657–1662). According to an exemplary embodiment, a probe based on a selected sequence, e.g., the wild-type sequence of MLip-1, is hybridized with a cDNA or other DNA product from a sample. The resulting duplex is treated with a DNA mismatch repair enzyme, and the cleavage products, if any, are detected using known electrophoresis or other polynucleotide separation protocols. See, e.g., U.S. Pat. No. 5,459,039.

In other embodiments, alterations in electrophoretic mobility are used to identify mutations in genes. For example, single strand conformation polymorphism (SSCP) can be used to detect differences in electrophoretic mobility between mutant and wild type nucleic acids, as described (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control nucleic acids are denatured and allowed to re-nature. Secondary structure of single-stranded nucleic acids varies according to their sequences, and the resulting alteration in electrophoretic mobility enables detection of sequence differences of as few as one nucleotide residue. The DNA fragments can be labeled or detected with labeled probes. The sensitivity of the assay can be enhanced using RNA (rather than DNA), because the secondary structure of RNA is more sensitive to sequence changes than that of DNA. In a preferred embodiment, heteroduplex analysis is used to separate double stranded heteroduplex molecules on the basis of changes in electrophoretic mobility, as described (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE; Myers et al. (1985) *Nature* 313:495). When DGGE is used as the method of analysis, DNA is modified to insure that it does not completely denature, for example by adding a 'GC clamp' of approximately 40 base pairs of high-melting GC-rich DNA by PCR. In another embodiment, a temperature gradient is used in place of a denaturant gradient to identify differences in the mobility of control and sample DNA, as described (Rosenbaum and Reissner (1987) *Biophys. Chem.* 265:12753).

Examples of other techniques for detecting point mutations include, but are not limited to, selective oligonucleotide hybridization, selective amplification, and selective primer extension. For example, oligonucleotide primers can be prepared in which the known mutation is located centrally. The primers are hybridized with target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides can be hybridized with PCR-amplified target DNA or with one of a number of mutant sequences when the oligonucleotides are attached to the hybridizing membrane and hybridized with labeled target DNA.

Alternatively, allele specific amplification (ASA) technology can be used to detect mutations in the MLip-1 gene. Oligonucleotides used as primers for ASA have an allele-specific (e.g. mutant allele-specific) sequence situated at the central portion of one or more primers. Amplification thus depends on hybridization of the primer(s) with the specific allele, as described (Gibbs et. al. (1989) *Nucleic Acids Res.* 17:2437–2448). Alternatively, ASA can be performed using an allele-specific sequence at the extreme 3' end of one primer such that, under appropriate conditions, mismatching prevents or reduces polymerase extension (Prossner (993) *Tibtech* 11:238). It can be desirable to introduce a novel restriction site in the region of an MLip-1 mutation to facilitate cleavage-based detection (Gasparini et al. (1992) *Mol. Cell Probes* 6:1). Amplification can be performed using Taq ligase for amplification (Barany (1991) *Proc. Natl. Acad. Sci. USA* 88:189). In such cases, ligation will occur only if there is a perfect match at the 3' end of the 5' sequence, thus making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be used (e.g., in clinical settings) to diagnose patients exhibiting symptoms or a family history of a disease or illness involving aberrant activity or expression of the MLip-1 gene. Furthermore, any cell type or tissue (e.g., a pancreatic tissue) in which MLip-1 protein is expressed can be utilized in the prognostic assays described herein.

3. Pharmacogenomics

Agents or modulators which have a stimulatory or inhibitory effect on activity or expression of MLip-1 protein, for example as identified by a screening assay described herein can be administered to patients to treat (prophylactically or therapeutically) disorders associated with aberrant activity or expression of MLip-1 protein. In conjunction with such treatment, pharmacogenomics of an individual (i.e., the relationship between the individual's genotype and the individual's response to a foreign compound or drug) can be considered. In general, two types of pharmacogenomic conditions can be differentiated. Genetic conditions transmitted as a single factor altering the way drugs act on the body are referred to as conditions which effect "altered drug action." Differences in metabolism of therapeutics can lead to toxicity, reduced therapeutic effectiveness, or therapeutic failure by altering the relation between dose and blood concentration of the pharmacologically active agent. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

Pharmacogenomic analysis of individuals permits selection of effective agents (e.g., drugs) for prophylactic or therapeutic treatments, based on the individual's genotype. Such pharmacogenomics can be used to determine appropriate dosages and therapeutic regimens for individuals. Accordingly, the activity of MLip-1 protein, expression of a nucleic acid encoding MLip-1 protein, or mutation content of the MLip-1 gene in an individual can be assessed in the presence of a variety of agents in order to select appropriate agent(s) for therapeutic or prophylactic treatment of the individual.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 {NAT 2} and cytochrome P450 enzymes CYP2D6 and CYP2C19) has provided an explanation of why some patients do not obtain expected drug effects or exhibit exaggerated drug responses or serious toxicity following administration of a the standard and safe dose of a drug. These polymorphisms occur as two phenotypes in the population, namely the extensive metabolizer (EM) and poor metabolizer (PM) phenotypes. The prevalence of PM varies among different populations. For example, the gene encoding CYP2D6 is highly polymorphic, and several mutations have been identified in PM, all of which result in absence of functional CYP2D6. Poor metabolizers of CYP2D6 and CYP2C 19 frequently experience exaggerated drug responses and side effects when they receive standard doses of drugs. If a metabolite is the active therapeutic moiety, a PM will exhibit no therapeutic response, as demonstrated for the analgesic effect of codeine mediated by CYP2D6-catalyzed generation of its metabolite, morphine. At the other extreme are the so called ultra-rapid metabolizers who do not respond to standard doses. Recently, the molecular basis of ultra-rapid metabolism has been determined to be CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenomic analysis can be used to predict an individual's drug responsiveness phenotype. This knowledge, when applied to dosing or drug selection, can avoid adverse reactions or therapeutic failure. Therapeutic or prophylactic efficiency can be thereby improved.

4. Monitoring of Effects During Clinical Trials

Monitoring the influence of agents (e.g., drug compounds) on expression or activity of MLip-1 protein (e.g., ability to modulate transmembrane transport of a fatty acyl moiety of a lipid or to hydrolyze or form ester bonds of a lipid) can be applied not only in basic drug screening, but also in clinical trials. For example, the effectiveness of an agent, as determined by a screening assay as described herein, to increase MLip-1 gene expression, protein level, or protein activity, can be monitored in clinical trials of subjects exhibiting decreased gene expression, protein level, or protein activity. Alternatively, the effectiveness of an agent, as determined by a screening assay, to decrease gene expression, protein level, or protein activity, can be monitored in clinical trials of subjects exhibiting increased gene expression, protein level, or protein activity.

For example, ability of an agent (e.g., compound, drug or small molecule) to modulate activity or expression of MLip-1 protein (e.g., as identified in a screening assay described herein) can be identified. Thus, in order to study the effect of agents on disorders relating to aberrant lipid metabolism, for example, in a clinical trial, cells can be isolated and RNA prepared and analyzed to determine the levels of expression of the MLip-1 gene or of another gene implicated in the disorder. The levels of gene expression (i.e., a gene expression pattern) can be quantified by Northern blot analysis or RT-PCR, as described herein, or alternatively by assessing the amount of MLip-1 protein produced, by one of the methods as described herein. The gene expression pattern can serve as a marker, indicative of the physiological response of the cells to the agent. Accordingly, this response marker can be assessed before, and at various points during, treatment of the individual with the agent in order to examine the effectiveness of the trial and, if desired, the necessity of altering the trial.

In one embodiment, the present invention includes a method for monitoring the effectiveness of treatment of a subject with an agent (e.g., an agonist, antagonist, peptidomimetic, protein, peptide, antibody substance, nucleic acid, small molecule, or other drug candidate identified by the screening assays described herein) comprising (i) obtaining a pre-administration sample from a subject prior to administration of the agent; (ii) detecting the level of a polypeptide or nucleic acid of the invention in the pre-administration sample; (iii) obtaining one or more post-administration samples from the subject; (iv) detecting the level the of the polypeptide or nucleic acid of the invention in the post-administration samples; (v) comparing the levels of the polypeptide or nucleic acid in the pre- and post-administration samples; and (vi) altering administration of the agent to the subject accordingly. For example, increased administration of the agent can be desirable to increase or decrease MLip-1 expression or activity (i.e., to increase the effectiveness of the agent).

D. Methods of Treatment

The present invention provides both prophylactic and therapeutic methods of treating a subject at risk for developing, susceptible to, or afflicted with a disorder associated with aberrant expression or activity of MLip-1 protein. Such disorders are described elsewhere in this disclosure.

1. Prophylactic Methods

In one aspect, the invention provides a method for preventing or inhibiting a disease or disorder associated with aberrant expression or activity of MLip-1 protein in a subject. The method comprises administering to the subject an agent that modulates expression or at least one activity of MLip-1 protein. Subjects at risk for a disease which is caused or contributed to by aberrant expression or activity of a polypeptide can be identified by, for example, any or a combination of diagnostic or prognostic assays as described herein. Administration of a prophylactic agent can occur prior to the manifestation of symptoms characteristic of the aberrance, such that a disease or disorder is prevented, inhibited in its progression, or inhibited in the severity of the disease or disorder. Depending on the type of aberrance, for example, an agonist or antagonist agent can be used for treating the subject. Selection of an appropriate agent can be made based on screening assays described herein.

2. Therapeutic Methods

In another aspect, the invention pertains to methods of modulating expression or activity of MLip-1 protein for therapeutic purposes. The modulatory method of the invention involves contacting a cell with an agent that modulates expression of MLip-1 protein or modulates one or more of the activities of MLip-1 protein. An agent that modulates expression or activity can be an agent as described herein, such as a nucleic acid or polypeptide of the invention, a peptidomimetic, an antibody substance, or a small molecule. In one embodiment, the agent stimulates one or more of the biological activities of MLip-1 protein. In another embodiment, the agent inhibits one or more biological activities of MLip-1 protein. Examples of such inhibitory agents include antisense nucleic acid molecules and antibodies. These modulatory methods can be performed in vitro (e.g., by culturing a cell with the agent) or, alternatively, in vivo (e.g., by administering the agent to a subject). As such, the present invention provides methods of treating an individual afflicted with a disease or disorder characterized by aberrant expression or activity of MLip-1 protein. In one embodiment, the method involves administering an agent (e.g., an agent identified by a screening assay described herein), or combination of agents that modulates (e.g., up-regulates or down-regulates) MLip-1 expression or activity. In another embodiment, the method involves administering a polypeptide of the invention, or a nucleic acid of the invention, as therapy to compensate for reduced or aberrant expression or activity of the polypeptide.

Stimulation of MLip-1 activity is desirable in situations in which activity or expression is abnormally low or down-regulated and/or in which increased activity is likely to have a beneficial effect, e.g., in pancreatic insufficiency disorders. Conversely, inhibition of MLip-1 activity is desirable in situations in which activity or expression is abnormally high or up-regulated and/or in which decreased activity is likely to have a beneficial effect.

The contents of all references, patents, and published patent applications cited in this disclosure are incorporated by reference.

Equivalents

Those skilled in the art will recognize, or be able to ascertain using no more than routine experimentation, many equivalents to the specific embodiments of the invention described herein. Such equivalents are encompassed by the following claims.

What is claimed is:

1. An isolated nucleic acid molecule having a nucleotide sequence which is at least 90% identical to the nucleotide sequence of either of SEQ ID NO: 1 or SEQ ID NO: 2, or a complement thereof, wherein the isolated nucleic acid molecule encodes a polypeptide that exhibits lipase activity.

2. The isolated nucleic acid molecule of claim 1, further comprising a vector nucleic acid sequence.

3. The isolated nucleic acid molecule of claim 1, further comprising a portion encoding a heterologous polypeptide.

4. A host cell which contains the nucleic acid molecule of claim 1.

5. The host cell of claim 4, wherein the host cell is a mammalian host cell.

6. A non-human mammalian host cell containing the nucleic acid molecule of claim 1.

7. A method for producing a polypeptide that exhibits lipase activity, the method comprising culturing the host cell of claim 4 under conditions in which the isolated nucleic acid molecule is expressed.

8. An isolated nucleic acid molecule which encodes a polypeptide comprising the amino acid sequence of SEQ ID NO: 3, or a complement thereof.

9. The isolated nucleic acid molecule of claim 8, further comprising a vector nucleic acid sequence.

10. The isolated nucleic acid molecule of claim 8, further comprising a portion encoding a heterologous polypeptide.

11. A host cell which contains the nucleic acid molecule of claim 8.

12. The host cell of claim 11, wherein the host cell is a mammalian host cell.

13. A non-human mammalian host cell containing the nucleic acid molecule of claim 8.

14. The isolated nucleic acid molecule of claim 8, comprising the nucleotide sequence of either of SEQ ID NO: 1 and SEQ ID NO: 2, or a complement thereof.

15. A method for producing a polypeptide that exhibits lipase activity, the method comprising culturing the host cell of claim 11 under conditions in which the isolated nucleic acid molecule is expressed.

16. A method for producing a polypeptide having the amino acid sequence of SEQ ID NO: 3, the method comprising culturing the host cell of claim 11 under conditions in which the nucleic acid molecule is expressed.

17. An isolated nucleic acid molecule comprising the nucleotide sequence of either of SEQ ID NO: 1 or SEQ ID NO: 2.

18. The isolated nucleic acid molecule of claim 17, further comprising a vector nucleic acid sequence.

19. The isolated nucleic acid molecule of claim 17, further comprising a portion encoding a heterologous polypeptide.

20. A host cell which contains the nucleic acid molecule of claim 17.

21. The host cell of claim 20, wherein the host cell is a mammalian host cell.

22. A non-human mammalian host cell containing the nucleic acid molecule of claim 17.

23. A method for producing a polypeptide that exhibits lipase activity, the method comprising culturing the host cell of claim 20 under conditions in which the molecule is expressed.

* * * * *